United States Patent
Weymouth-Wilson et al.

(10) Patent No.: US 10,301,350 B2
(45) Date of Patent: May 28, 2019

(54) 6-ALKYL-7-HYDROXY-4-EN-3-ONE STEROIDS AS INTERMEDIATES FOR THE PRODUCTION OF STEROIDAL FXR MODULATORS

(71) Applicant: NZP UK LIMITED, Reading, Berkshire (GB)

(72) Inventors: Alexander Weymouth-Wilson, Reading (GB); Zofia Komsta, Reading (GB); James Boydell, Reading (GB); Carl Otter, Reading (GB); Laura Wallis, Reading (GB); Rhys Batchelor, Reading (GB)

(73) Assignee: NZP UK LIMITED, Bristol (GB)

( * ) Notice: Subject to any disclaimer, the term of this patent is extended or adjusted under 35 U.S.C. 154(b) by 0 days.

(21) Appl. No.: 15/528,214

(22) PCT Filed: Nov. 19, 2015

(86) PCT No.: PCT/GB2015/053516
§ 371 (c)(1),
(2) Date: May 19, 2017

(87) PCT Pub. No.: WO2016/079517
PCT Pub. Date: May 26, 2016

(65) Prior Publication Data
US 2017/0327528 A1    Nov. 16, 2017

(30) Foreign Application Priority Data

Nov. 19, 2014  (GB) .................................. 1420593.4
Nov. 19, 2014  (GB) .................................. 1420594.2
Apr.  1, 2015   (GB) .................................. 1505670.8

(51) Int. Cl.
   *C07J 9/00*     (2006.01)
   *C07J 71/00*    (2006.01)

(52) U.S. Cl.
   CPC ............ *C07J 9/005* (2013.01); *C07J 71/001* (2013.01)

(58) Field of Classification Search
   CPC .............................. C07J 9/005; C07J 71/001
   See application file for complete search history.

(56) References Cited

U.S. PATENT DOCUMENTS

| | | |
|---|---|---|
| 2,624,748 A | 1/1953 | Levin et al. |
| 4,289,872 A | 9/1981 | Denkewalter et al. |
| 5,229,490 A | 7/1993 | Tam |
| 5,643,575 A | 7/1997 | Martinez et al. |
| 5,932,462 A | 8/1999 | Harris et al. |
| 2003/0143596 A1 | 7/2003 | Bentley et al. |
| 2008/0214515 A1 | 9/2008 | Ferrari et al. |
| 2009/0062256 A1 | 5/2009 | Olson |
| 2010/0063018 A1 | 3/2010 | Pellicciari et al. |
| 2011/0263555 A1 | 10/2011 | Pellicciari |
| 2014/0148428 A1 | 5/2014 | Pruzanski et al. |
| 2014/0206657 A1 | 7/2014 | Yu et al. |

FOREIGN PATENT DOCUMENTS

| | | | |
|---|---|---|---|
| CN | 106279328 A | 1/2017 | |
| CN | 106397522 A | 2/2017 | |
| CN | 106478756 A | 3/2017 | |
| CN | 106478759 A | 3/2017 | |
| CN | 106518946 A | 3/2017 | |
| EP | 1568706 A1 | 8/2005 | |
| EP | 1985621 A1 | 10/2008 | |
| EP | 1985621 A1 * | 10/2008 | ............. C07J 9/005 |
| WO | WO93/21259 A1 | 10/1993 | |
| WO | WO94/19366 A1 | 9/1994 | |
| WO | WO96/21469 A1 | 7/1996 | |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Akhrem, Total Synthesis of Steroids,1970, Plenum Press, New York, pp. vii-362. (Year: 1970).*
Verlarde et al, Journal of Organic Chemistry, Steroids. CXIII.1 6-Methyl Estrogens, 1959, pp. 311-313. (Year: 1959).*
International Search Report for PCT/GB2015/053516 dated Feb. 11, 2016, 4 pages.
Written Opinion of the ISA for PCT/GB2015/053516 dated Feb. 11, 2016, 8 pages.
Uekawa et al., "Short-step Synthesis of Chenodiol from Stigmasterol", Bioscience Biotechnology Biochemistry, Japan Society for Bioscience, Biotechnology, and Agrochemistry, vol. 68, No. 6, Jan. 1, 2004, pp. 1332-1337.

(Continued)

*Primary Examiner* — Paul A Zucker
(74) *Attorney, Agent, or Firm* — Morgan, Lewis & Bockius, LLP

(57) ABSTRACT

The invention relates to compounds of formula (I) and related methods, wherein $R^1$, $R^2$, Y, $R^4$ and $R^5$ are as defined herein. The compounds are intermediates in the synthesis of synthetic bile acids with pharmacological activity. The invention futher provides intermediated in the systhesis of obeticholic acid and its analogues. The invention also provides methods related to the synthesizing of these intermediates and methods of preparing obeticholic acid and obeticholic acid analogues from the compound of the invention.

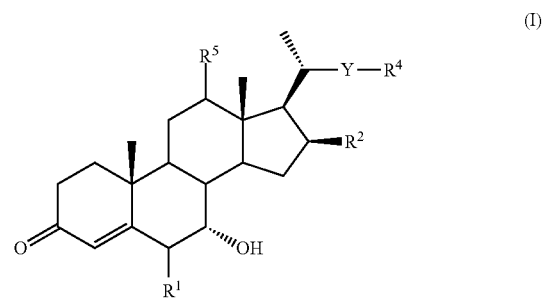

(I)

18 Claims, 2 Drawing Sheets

(56) References Cited

FOREIGN PATENT DOCUMENTS

| | | |
|---|---|---|
| WO | WO02/072598 A1 | 9/2002 |
| WO | 2005/082925 A2 | 9/2005 |
| WO | WO 2006/122977 | 11/2006 |
| WO | WO2006/122977 A2 | 11/2006 |
| WO | 2007/095174 A2 | 8/2007 |
| WO | WO2008/002573 A2 | 1/2008 |
| WO | 2008/091540 A2 | 7/2008 |
| WO | WO2010/014836 A2 | 2/2010 |
| WO | 2010/059853 A1 | 5/2010 |
| WO | WO 2010/059859 | 5/2010 |
| WO | WO2010/059859 A1 | 5/2010 |
| WO | WO2011/014661 A2 | 2/2011 |
| WO | WO2013/192097 A1 | 12/2013 |
| WO | WO2014/066819 A1 | 5/2014 |
| WO | 2014/085474 A1 | 6/2014 |
| WO | 2014/184271 A1 | 11/2014 |
| WO | WO2014/188377 A2 | 11/2014 |
| WO | 2015/181275 A1 | 5/2015 |
| WO | WO2015/183794 A1 | 12/2015 |
| WO | 2016/073767 A1 | 5/2016 |
| WO | WO 2016/079518 | 5/2016 |
| WO | WO2016/079518 A1 | 5/2016 |
| WO | WO 2016/079519 | 5/2016 |
| WO | WO2016/079519 A1 | 5/2016 |
| WO | WO 2016/079520 | 5/2016 |
| WO | WO2016/079520 A1 | 5/2016 |
| WO | 2016/086115 A1 | 6/2016 |
| WO | 2016/086134 A1 | 6/2016 |
| WO | 2016/086169 A1 | 6/2016 |
| WO | 2016/086218 A1 | 6/2016 |
| WO | 2016/205475 A2 | 12/2016 |

OTHER PUBLICATIONS

Verlarde et al., "Steroids. CXIII. 6-Methyl Estrogens", The Journal of Organic Chemistry, vol. 24, No. 3, Mar. 1, 1959, pp. 311-313.
Leppik R.A., Improved synthesis of 3-keto, 4-ene-3-keto, and 4,6-diene-3-keto bile acids, Steroids, 1983, 41(4), pp. 475-484 (1983).
Usui et al., Metabolic studies of bile acids. XLV1. The transformation of 3β,-7α-dihydroxychol-5-enic-24-14C acid to chenodeoxycholic acid in the rat. The significance of the C-7α-hydroxyl group in bile acid formation, Steroids, 1964, (3)2, pp. 147-161 (1964).
Dong Hui et al., A Short and Highly Stereoselective Synthesis of Squalamine from Methyl Chenodeoxycholanate, Chin. J. Chem., 2005, 23(2), pp. 176-181 (2005).
Uekawa et al., Short-step Synthesis of Chenodiol from Stigmasterol, Biosci. Biotechnol. Biochem., 2004, 68(6), pp. 1332-1337 (2004).
Esperanza et al., Steroids. CXIII. 6-Methyl Estrogens, J. Org. Chem., 1959, 24(3) pp. 311-313 (1959).
Jonker et al., FXR and PXR: Potential therapeutic targets in cholestasis, J. Steroid Biochem., Mol. Biol., 2012, 130, pp. 147-158 (2012).
Paulekuhn et al., Trends in Active Pharmaceutical Ingredient Salt Selection based on Analysis of the Orange Book Database, J. Med. Chem, 2007, 50(26), pp. 6665-6672 (2007).
Festa et al., Exploitation of Cholane Scaffold for the Discovery of Potent and Selective Farnesoid X Receptor (FXR) and G-Protein Coupled Bile Acid Receptor 1 (GP-BAR1) Ligands, J Med. Chem., 2014, 57(20), pp. 8477-8495 (2014).
Bortolini et al., Improved Enantioselectivity in the Epoxidation of Cinnamic Acid Derivatives with Dioxiranes from Keto Bile Acids, J. Org. Chem, 2002, 67(16), pp. 5802-5806 (2002).
Classon et al., New halogenation reagent systems useful for the mild one-step conversion of alcohols into iodides or bromides, J. Org. Chem, 1988, (53)26, pp. 6126-6130 (1988).
Pellicari et al., Novel stereoselective synthesis and chromatographic evaluation of E-guggulsterone, Steroids, 2012, 77(3), pp. 250-254 (2012).
Dauben et al., Stereocontrolled Synthesis of Steroidal Side Chains, J. Am. Chem, 1981, 103(1), pp. 237-238 (1981).
Marker et al., Sterols. CII. Chlorogenin, J. Am. Chem. Soc., 1940, 62(9), pp. 2537-2540 (1940).
Shepherd et al., A Synthesis of Progesterone from Ergosterol, J. Am Chem. Soc., 1955, 77(5), pp. 1212-1215 (1955).
Goldstein, Synthesis and Bioevaluation of Δ7-5-Desaturase Inhibitors, an Enzyme Late in the Biosynthesis of the Fungal Sterol Ergosterol, J. Med. Chem, 1996, 39(26), pp. 5092-5099 (1996).
Zhou et al., A stereoselective synthesis of squalamine, Tetrahedron, 2002, 58, pp. 10293-10299 (2002).
Carnell et al., Design, Synthesis, and In Vitro Testing of α-Methylacyl-CoA Racemase Inhibitors, J. Med. Chem., 2007, 50(11), pp. 2700-2707 (2007).
Zeng et al., Neurosteroid Analogues. 10. The Effect of Methyl Group Substitution at the C-6 and C-7 Positions on the GABA Modulatory and Anesthetic Actions of (3α,5α)- and (3α,5β)-3-Hydroxypregnan-20-one, J. M. Chem., 2005, 48(8), pp. 3051-3059 (2005).
Wang et al., "Targeting enterohepatic bile acid signaling as a novel approach to modulate hepatic autophagic activity in maintaining cholesterol homeostasis," Hepatology (Oct. 2015), 62 (S1), 280A.

\* cited by examiner

6-ALKYL-7-HYDROXY-4-EN-3-ONE STEROIDS AS INTERMEDIATES FOR THE PRODUCTION OF STEROIDAL FXR MODULATORS

This application is the U.S. national phase of International Application No. PCT/GB2015/053516 filed Nov. 19, 2015 which designated the U.S. and claims priority to GB Patent Application No. 1420593.4 filed Nov. 19, 2014, GB Patent Application No. 1420594.2 filed Nov. 19, 2014 and GB 1505670.8 filed Apr. 1, 2015, the entire contents of each of which are hereby incorporated by reference.

The present invention relates to compounds which are intermediates in the synthesis of bile acid derivatives with pharmacological activity. In particular, the invention relates to intermediates in the synthesis of obeticholic acid and its analogues. In addition, the invention relates to a method of synthesizing these intermediates and a method of preparing obeticholic acid and obeticholic acid analogues from the compounds of the invention.

Bile acids are steroid acids which are found in the bile of mammals and include compounds such as cholic acid, chenodeoxycholic acid, lithocholic acid and deoxycholic acid, all of which are found in humans. Many bile acids are natural ligands of the farnesoid X receptor (FXR) which is expressed in the liver and intestine of mammals, including humans.

Bile acids are derivatives of steroids and are numbered in the same way. The following shows the general numbering system for steroids and the numbering of the carbon atoms in chenodeoxycholic acid.

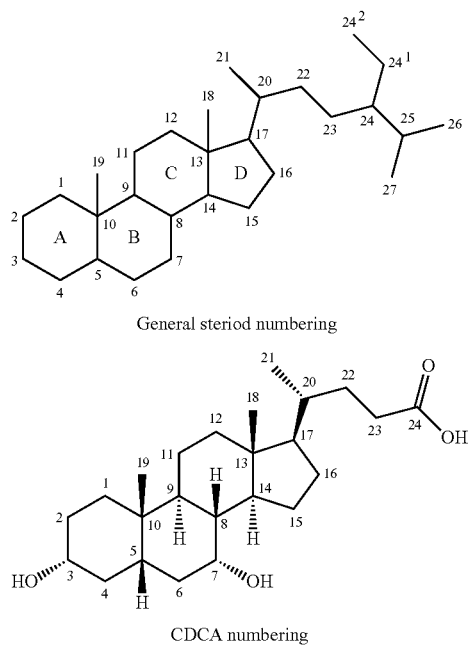

General steriod numbering

CDCA numbering

Agonists of FXR have been found to be of use in the treatment of cholestatic liver disorders including primary biliary cirrhosis and non-alcoholic steatohepatitis (see review by Jonker et al, in *Journal of Steroid Biochemistry & Molecular Biology,* 2012, 130, 147-158).

Ursodeoxycholic acid (UDCA), a bile acid originally isolated from the gall bladder of bears, is currently used in the treatment of cholestatic liver disorders, although it appears to be inactive at the FXR.

As well as their action at the FXR, bile acids and their derivatives are also modulators of the G protein-coupled receptor TGR5. This is a member of the rhodopsin-like superfamily of G-protein coupled receptors and has an important role in the bile acid signalling network, which complements the role of the FXR.

Because of the importance of FXR and TGR5 agonists in the treatment of cholestatic liver disorders, efforts have been made to develop new compounds which have agonist activity at these receptors. One particularly active compound is obeticholic acid, which is a potent agonist of both FXR and TGR5. Obeticholic acid is described in WO 02/072598 and EP1568706, both of which describe a process for the preparation of obeticholic acid from 7-keto lithocholic acid, which is derived from cholic acid. Further processes for the production of obeticholic acid and its derivatives are described in WO 2006/122977, US 2009/0062256 and WO 2013/192097 and all of these processes also start from 7-keto lithocholic acid.

It is clear from the number of patent publications directed to processes for the production of obeticholic acid that it is by no means simple to synthesise this compound and indeed the process which is currently used starts from cholic acid, has 12 steps and a low overall yield.

In addition to the inefficiency and high cost of this process, there are also problems with the cost and availability of the starting materials. Cholic acid, the current starting material for the production of obeticholic acid, is a natural bile acid which is usually obtained from the slaughter of cows and other animals. This means that the availability of cholic acid and other bile acids is limited by the number of cattle available for slaughter. Since the incidence of cholestatic liver disease is increasing worldwide, the demand for synthetic bile acids such as obeticholic acid is also likely to increase and it is doubtful whether the supply of naturally derived bile acids will continue to be sufficient to meet demand.

Furthermore, the use of a starting material derived from animals means that there is the possibility of the contamination of the material with infectious agents such as viruses or prions, which can not only be hazardous to workers but could potentially contaminate the end products if steps are not taken to prevent this.

Although some patients with cholestatic liver disease can be treated with ursodeoxycholic acid, this is also a natural bile acid and faces the same problems of limited availability and high cost.

In an attempt to solve the problems associated with the use of bile acids as starting materials, the present inventors have devised a process for the synthesis of synthetic bile acid derivatives, such as obeticholic acid, which uses plant sterols as starting materials.

The inventors have developed a process for the production of synthetic bile acids which proceeds via novel intermediates and which provides the final product in significantly higher yield than current processes. The process is flexible and can use a variety of different starting materials including animal, fungal and plant sterols.

Suitable animal sterols which can be used as starting materials include deoxycholic acid, cholic acid, while fungal sterols include ergosterol.

Plant sterols are widely available at significantly lower cost than bile acids and, indeed, are often waste products of other processes. Suitable plant sterol and plant sterol derivatives which can be used as starting materials include bisnorcholenol (also known as 20-hydroxymethylpregn-4-en-3-one), androstenedione, androstenedienedione, dehydroepiandrosterone, stigmasterol, brassicasterol, campesterol and β-sitosterol.

The present invention relates to intermediates in the novel process as well as to processes for preparing the intermediates and processes for converting them to the desired products.

Therefore, in a first aspect of the present invention there is provided a compound of general formula (I):

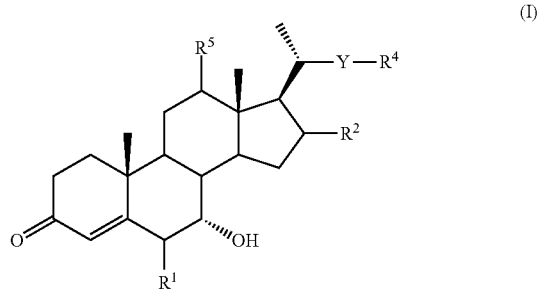

(I)

wherein:
$R^1$ is $C_{1-4}$ alkyl optionally substituted with one or more substituents selected from halo, $OR^6$ or $NR^6R^7$;
where each of $R^6$ and $R^7$ is independently selected from H or $C_{1-4}$ alkyl;
$R^2$ is H, halo or OH or a protected OH;
Y is a bond or an alkylene, alkenylene or alkynylene linker group having from 1 to 20 carbon atoms and optionally substituted with one or more groups $R^3$;
each $R^3$ is independently halo, $OR^8$ or $NR^8R^9$;
where each of $R^8$ and $R^9$ is independently selected from H or $C_{1-4}$ alkyl; and
$R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$; $SO_3R^{10}$, or $OSO_3R^{10}$;
where each $R^{10}$ and $R^{11}$ is independently:
a. hydrogen or
b. $C_{1-20}$ alkyl, $C_{2-20}$ alkenyl, $C_{2-20}$ alkynyl, —O—$C_{1-20}$ alkyl, —O—$C_{2-20}$ alkenyl or —O—$C_{2-20}$ alkynyl, any of which is optionally substituted with one or more substituents selected from halo, $NO_2$, CN, $OR^{19}$, $SR^{19}$, $SO_2R^{19}$, $SO_3R^{19}$ or $N(R^{19})_2$, or a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$; or
c. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;
d. a polyethylene glycol residue;
each $R^{19}$ is independently selected from H, $C_{1-6}$ alkyl, $C_{1-6}$ haloalkyl, or a 6- to 14-membered aryl or 5 to 14-membered heteroaryl group either of which is optionally substituted with halo, $C_{1-6}$ alkyl or $C_{1-6}$ haloalkyl;
each $R^{13}$ is independently
a. $C_{1-20}$ alkyl, $C_{2-20}$ alkenyl or $C_{2-20}$ alkynyl optionally substituted with one or more substituents selected from halo, $NO_2$, CN, $OR^{19}$, $SR^{19}$, $SO_2R^{19}$, $SO_3R^{19}$ or $N(R^{19})_2$, a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; or
b. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;
each $R^{19}$ is independently selected from H, $C_{1-6}$ alkyl or $C_{1-6}$ haloalkyl;
$R^5$ is H or OH or a protected OH;
or a salt or an isotopic variant thereof.

Compounds of general formula (I) are intermediates in the synthesis of pharmaceutically active compounds such as obeticholic acid and its derivatives.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All publications, including but not limited to patents and patent applications, cited in this specification are herein incorporated by reference as if each individual publication were specifically and individually indicated to be incorporated by reference herein as though fully set forth.

In the present application the term "$C_{1-20}$" alkyl refers to a straight or branched fully saturated hydrocarbon group having from 1 to 20 carbon atoms. The term encompasses methyl, ethyl, n-propyl, isopropyl, n-butyl, isobutyl and t-butyl. Other alkyl groups, for example $C_{1-20}$ alkyl, $C_{1-6}$ alkyl or $C_{1-3}$ alkyl are as defined above but contain different numbers of carbon atoms.

The term "$C_{1-6}$ haloalkyl" refers to a straight or branched alkyl group as defined above having from 1 to 6 carbon atoms and substituted with one or more halo atoms, up to perhalo substitution. Examples include trifluoromethyl, chloroethyl and 1,1-difluoroethyl.

The term "$C_{2-20}$ alkenyl" refers to a straight or branched hydrocarbon group having from 2 to 20 carbon atoms and at least one carbon-carbon double bond. Examples include ethenyl, prop-1-enyl, hex-2-enyl etc.

The term "$C_{2-20}$ alkynyl" refers to a straight or branched hydrocarbon group having from 2 to 20 carbon atoms and at least one carbon-carbon triple bond. Examples include ethynyl, prop-1-ynyl, hex-2-ynyl etc.

The term "alkylene" refers to a straight or branched fully saturated hydrocarbon chain. Examples of alkylene groups include —$CH_2$—, —$CH_2CH_2$—, $CH(CH_3)$—$CH_2$—, $CH_2CH(CH_3)$—, —$CH_2CH_2CH_2$—, —$CH_2CH(CH_2CH_3)$— and —$CH_2CH(CH_2CH_3)CH_2$—.

The term "alkenylene" refers to a straight or branched hydrocarbon chain containing at least one carbon-carbon double bond. Examples of alkenylene groups include —CH=CH—, —CH=C(CH_3)—, —$CH_2$CH=CH—, —CH=CHCH_2—, $CH_2CH_2$CH=CH—, $CH_2$CH=C(CH_3)— and —$CH_2$CH=C(CH_2CH_3)—.

The term "alkynylene" refers to a straight or branched hydrocarbon chain containing at least one carbon-carbon triple bond. Examples of alkenylene groups include —C≡C—, —$CH_2$C≡C—, —C≡C—$CH_2$—, $CH_2CH_2$C≡C—, $CH_2$C≡CCH_2— and —$CH_2$CH—C≡$CH_2CH_2$—.

The terms "aryl" and "aromatic" refer to a cyclic group with aromatic character having from 6 to 14 ring carbon atoms (unless otherwise specified) and containing up to three rings. Where an aryl group contains more than one ring, not all rings must be aromatic in character. Examples include phenyl, naphthyl and anthracenyl as well as partially saturated systems such as tetrahydronaphthyl, indanyl and indenyl.

The terms "heteroaryl" and "heteroaromatic" refer to a cyclic group with aromatic character having from 5 to 14 ring atoms (unless otherwise specified), at least one of which is a heteroatom selected from N, O and S, and containing up to three rings. Where a heteroaryl group contains more than one ring, not all rings must be aromatic in character. Examples of heteroaryl groups include pyridine, pyrimidine, indole, benzofuran, benzimidazole and indolene.

The term "halogen" refers to fluorine, chlorine, bromine or iodine and the term "halo" to fluoro, chloro, bromo or iodo groups.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

Polyethylene glycol (PEG) is a polyether compound, which in linear form has general formula H—[O CH$_2$—CH$_2$]$_n$—OH. A polyethylene glycol residue is a PEG in which the terminal H is replaced by a bond linking it to the remainder of the molecule.

Branched versions, including hyperbranched and dendritic versions are also contemplated and are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly (ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; US 2003/0143596; WO 96/21469; and WO 93/21259 may also be used.

The PEG polymers may have an average molecular weight of, for example, 600-2,000,000 Da, 60,000-2,000,000 Da, 40,000-2,000,000 Da, 400,000-1,600,000 Da, 800-1,200,000 Da, 600-40,000 Da, 600-20,000 Da, 4,000-16,000 Da, or 8,000-12,000 Da.

The term "protected OH" relates to an OH group protected with any suitable protecting group. For example, the protected OH may be a group $R^4$ as defined above.

Suitable protecting groups include esters such that, for example when $R^2$ and/or $R^5$ is a protected OH, $R^2$ and/or $R^5$ may independently be a group OC(O)$R^{14}$, where $R^{14}$ is a group $R^{10}$ as defined above. Silyl ethers are also suitable, and in this case, $R^2$ and/or $R^5$ may independently be a group OSi($R^{16}$)$_3$, where each $R^{16}$ is independently a group $R^{13}$ as defined above.

Other suitable protecting groups for OH are well known to those of skill in the art (see Wuts, PGM and Greene, TWh(2006) "Greene's Protective Groups in Organic Synthesis", 4$^{th}$ Edition, John Wiley & Sons, Inc., Hoboken, N.J., USA).

References to a protecting group which is stable in basic conditions mean that the protecting group cannot be removed by treatment with a base.

Appropriate salts of the compounds of general formula (I) include basic addition salts such as sodium, potassium, calcium, aluminium, zinc, magnesium and other metal salts as well as choline, diethanolamine, ethanolamine, ethyl diamine, meglumine and other well-known basic addition salts as summarised in Paulekuhn et al., *J. Med. Chem.* 2007, 50, 6665-6672 and/or known to those skilled in the art.

In some suitable compounds, the compound of general formula (I) is a compound of general formula (IA):

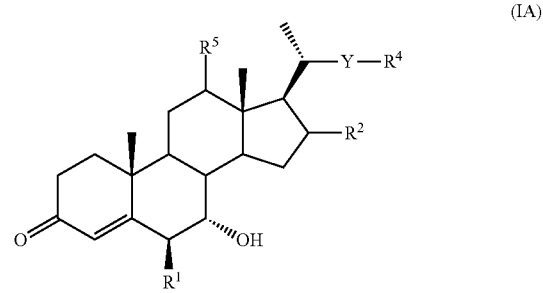

(IA)

wherein $R^1$, $R^2$, Y, $R^4$ and $R^5$ are as defined for general formula (I).

In some suitable compounds of general formula (I) and (IA):

$R^1$ is $C_{1-4}$ alkyl optionally substituted with one or more substituents selected from halo, $OR^6$ or $NR^6R^7$;
  where each of $R^6$ and $R^7$ is independently selected from H or $C_{1-4}$ alkyl;

$R^2$ is H, halo or OH;

Y is a bond or an alkylene or alkenylene linker group having from 1 to 6 carbon atoms and optionally substituted with one or more group $R^3$;

each $R^3$ is independently halo, $OR^8$ or $NR^8R^9$;
  where each of $R^8$ and $R^9$ is independently selected from H or $C_{1-4}$ alkyl;

$R^4$ is C(O)$OR^{10}$, C(O)$NR^{10}R^{11}$, S(O)$R^{10}$, SO$_2R^{10}$, OSO$_2R^{10}$, SO$_3R^{10}$, or OSO$_3R^{10}$; or $R^4$ is C(O)$OR^{10}$, C(O)$NR^{10}R^{11}$, S(O)$R^{10}$, SO$_2R^{10}$, or OSO$_2R^{10}$;
  where, in either case, each $R^{10}$ is hydrogen or $C_{1-6}$ alkyl or benzyl, either of which may optionally be substituted with one or more halo substituents and $R^{11}$ is hydrogen or $C_{1-6}$ alkyl, benzyl, —$C_{1-4}$ alkylene-SO$_3$H or —$C_{1-4}$ alkylene-SO$_3$($C_{1-4}$ alkyl), any of which may optionally be substituted with one or more halo substituents.

In suitable compounds of general formulae (I) and (IA), $R^1$ may be $C_{1-4}$ alkyl optionally substituted with one or more substituents selected from halo, $OR^6$ or $NR^6R^7$, where $R^6$ and $R^7$ are each independently H, methyl or ethyl, especially H or methyl.

More suitably, $R^1$ is unsubstituted $C_{1-4}$ alkyl.

In particularly suitable compounds, $R^1$ is ethyl.

In some compounds of general formula (I) and (IA), Y is a bond.

Suitably in compounds of general formulae (I) and (IA), Y is an alkylene or alkenylene linker group having from 1 to 15 carbon atoms, more suitably 1 to 12, 1 to 10 or 1 to 8 carbon atoms and optionally substituted with one or more groups $R^3$ as defined above. Typically each $R^3$ is independently halo, $OR^8$ or $NR^8R^9$; where each of $R^8$ and $R^9$ is independently selected from H, methyl or ethyl, especially H or methyl.

In some suitable compounds, Y is an unsubstituted alkylene or alkenylene linker having from 1 to 15 carbon atoms, more suitably 1 to 12, 1 to 10 or 1 to 8 carbon atoms.

In some suitable compounds of general formula (I), $R^2$ is H.

In other suitable compounds of general formula (I), $R^2$ is OH.

In still other suitable compounds of general formula (I), $R^2$ is a protected OH group. When $R^2$ is a protected OH group, it may be a group which is not stable in a basic environment such that treatment with a base converts the protected OH group to OH. Examples of such groups are well known in the art and include a group $OC(O)R^{14}$ as defined above in which $R^{14}$ is a group $R^{10}$ as defined above for general formula (I).

Particularly suitable $R^{14}$ groups are as defined for $R^{10}$ below.

Alternatively, $R^2$ may be a protected OH group which is stable in a basic environment. Examples of such groups include $OSi(R^{16})_3$, where each $R^{16}$ is independently a group $R^{13}$ as defined above.

Particularly suitable $R^{16}$ groups are as defined for $R^{13}$ below.

In the compounds of general formulae (I) and (IA) $R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, or $OSO_3R^{10}$ Suitably, is $C(O)OR^{10}$, $OR^{10}$, $SO_3R^{10}$, or $OSO_3R^{10}$ More suitably, $R^4$ is $C(O)OR^{10}$, $SO_3R^{10}$, or $OSO_3R^{10}$ Suitably, each $R^{10}$ and $R^{11}$ is independently:
a. hydrogen or
b. $C_{1-10}$ alkyl, $C_{2-10}$ alkenyl, $C_{2-10}$ alkynyl, —O—$C_{1-10}$ alkyl, —O—$C_{2-10}$ alkenyl or —O—$C_{2-10}$ alkynyl, any of which is optionally substituted with one or more substituents as described above; or
c. a 6- to 10-membered aryl or 5 to 10-membered heteroaryl group optionally substituted with one or more substituents as described above.
d. a polyethylene glycol residue.

More suitably, each $R^{10}$ and $R^{11}$ is independently
a. hydrogen or
b. $C_{1-10}$ alkyl, $C_{2-10}$ alkenyl, $C_{2-10}$ alkynyl or —O—$C_{1-10}$ alkyl optionally substituted with one or more substituents as described above or
c. a 6- to 10-membered aryl group optionally substituted with one or more substituents as described above.

Suitably each $R^{13}$ is independently selected from:
a. $C_{1-10}$ alkyl, $C_{2-10}$ alkenyl or $C_{2-10}$ alkynyl optionally substituted with one or more substituents as described above; or
b. a 6- to 10-membered aryl or 5 to 10-membered heteroaryl group optionally substituted with one or more substituents as described above.

More suitably, each $R^{13}$ is independently selected from:
a. $C_{1-10}$ alkyl, $C_{2-10}$ alkenyl or $C_{2-10}$ alkynyl optionally substituted with one or more substituents as described above; or
b. a 6- to 10-membered aryl group optionally substituted with one or more substituents as described above.

Still more suitably, each $R^{13}$ is independently selected from $C_{1-10}$ alkyl or phenyl, either of which is optionally substituted as described above.

Suitable substituents for alkyl, alkenyl, alkynyl, alkoxy, alkenyloxy and alkynyloxy $R^{10}$ and $R^{11}$ groups and alkyl, alkenyl and alkynyl $R^{13}$ groups include halo, $NO_2$, CN, $OR^{19}$, $SR^{19}$, $SO_2R^{19}$, $SO_3R^{19}$ or $N(R^{19})_2$, or a 6- to 10-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; where $R^{19}$ is as defined above.

More suitable substituents for these $R^{10}$, $R^{11}$ and $R^{13}$ groups include halo, $OR^{19}$, $N(R^{19})_2$ or a 6- to 10-membered aryl group optionally substituted as described above, more suitably optionally substituted with halo, $C_{1-4}$ alkyl, $C_{1-4}$ haloalkyl, —O—$C_{1-4}$ alkyl, —O—$C_{1-4}$ haloalkyl, —NH($C_{1-4}$ alkyl) or —N($C_{1-4}$ alkyl)$_2$; for example fluoro, chloro, methyl, ethyl, trifluoromethyl, methoxy, ethoxy, trifluoromethoxy, amino, methyl amino and dimethylamino.

Suitable substituents for aryl and heteroaryl $R^{10}$, $R^{11}$ and $R^{13}$ groups include $C_{1-6}$ alkyl, $C_{1-6}$ haloalkyl, halo, $NO_2$, CN, $OR^{19}$, $SR^{19}$ or $N(R^{19})_2$.

More suitable substituents for these $R^{10}$, $R^{11}$ and $R^{13}$ groups include $C_{1-4}$ alkyl, $C_{1-4}$ haloalkyl, halo, $OR^{19}$ or $N(R^{19})_2$; in particular, halo, $C_{1-4}$ alkyl, $C_{1-4}$ haloalkyl, —O—$C_{1-4}$ alkyl, —O—$C_{1-4}$ haloalkyl, —NH($C_{1-4}$ alkyl) or —N($C_{1-4}$ alkyl)$_2$.

Specific examples of substituents for aryl and heteroaryl $R^{10}$, $R^{11}$ and $R^{13}$ groups include fluoro, chloro, methyl, ethyl, trifluoromethyl, methoxy, ethoxy, trifluoromethoxy, amino, methyl amino and dimethylamino.

As set out above, each $R^{19}$ is independently selected from H, $C_{1-6}$ alkyl, $C_{1-6}$ haloalkyl, or a 6- to 14-membered aryl or 5 to 14-membered heteroaryl group either of which is optionally substituted with one or more halo, $C_{1-6}$ alkyl or $C_{1-6}$ haloalkyl substituents.

Suitably, $R^{19}$ is H, $C_{1-6}$ alkyl, $C_{1-6}$ haloalkyl, or a 6- to 10-membered aryl or 5 to 10-membered heteroaryl group optionally substituted with one or more halo, $C_{1-4}$ alkyl or $C_{1-4}$ haloalkyl substituents.

More suitably, $R^{19}$ is H, $C_{1-6}$ alkyl, $C_{1-6}$ haloalkyl or phenyl optionally substituted with one or more halo, $C_{1-4}$ alkyl or $C_{1-4}$ haloalkyl substituents.

Specific examples of $R^{19}$ include H, methyl, ethyl, trifluoromethyl or phenyl optionally substituted with one or more fluoro, chloro, methyl, ethyl or trifluoromethyl groups.

In some suitable compounds of general formula (I), $R^5$ is H.

In other suitable compounds of general formula (I), $R^5$ is OH.

In still other suitable compounds of general formula (I), $R^5$ is a protected OH group.

In still other suitable compounds of general formula (I), $R^5$ is a protected OH group. When $R^5$ is a protected OH group, it may be a group which is not stable in a basic environment such that treatment with a base converts the protected OH group to OH. Examples of such groups are well known in the art and include a group $OC(O)R^{14}$ as defined above in which $R^{14}$ is a group $R^{10}$ as defined above for general formula (I).

Particularly suitable $R^{14}$ groups are as defined for $R^{10}$ above.

Alternatively, $R^5$ may be a protected OH group which is stable in a basic environment. Examples of such groups include $OSi(R^{16})_3$, where each $R^{16}$ is independently a group $R^{13}$ as defined above.

Particularly suitable $R^{16}$ groups are as defined for $R^{13}$ above.

In some suitable compounds of general formulae (I) and (IA), independently or in any combination:

Y is a bond or an alkylene or alkenylene group having 1 to 3 carbon atoms and is optionally substituted with one or two $R^3$ groups;

$R^4$ is $C(O)OR^{10}$, $SO_3R^{10}$, or $OSO_3R^{10}$, where $R^{10}$ is as defined above but is more suitably H, $C_{1-6}$ alkyl or benzyl; and $R^5$ is H or OH.

In some more suitable compounds, independently or in any combination:

$R^1$ is ethyl; and/or $R^2$ is H; and/or

Y is a bond, —$CH_2$—, —$CH_2CH_2$—, —CH=CH— or —CH=C(CH$_3$)—; and/or $R^4$ is $C(O)OR^{10}$, where $R^{10}$ is H, $C_{1-6}$ alkyl or benzyl; and/or $R^5$ is H.

In some particularly suitable compounds of this type, $R^1$ is ethyl and/or $R^{10}$ is $C_{1-6}$ alkyl or benzyl.

Particularly suitable compounds of the present invention include (6β, 7α, 22E)-6-ethyl-7-hydroxy-3-oxo-4,22-choladien-24-oic acid;

(6β, 7α)-6-ethyl-7-hydroxy-3-oxo-4-cholen-24-oic acid and $C_{1-6}$ alkyl and benzyl esters thereof and salts thereof, especially the methyl and ethyl esters.

Compounds of general formula (I) and (IA) may be prepared from compounds of general formula (II):

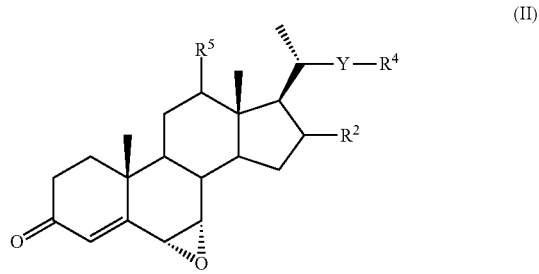

(II)

wherein $R^2$, $R^4$, $R^5$ and Y are as defined in general formula (I);

by selective alkylation with an organometallic reagent.

Suitable organometallic reagents include Gilman reagents formed by reaction of an alkyl lithium compound of formula (XXIV):

$R^1$—Li          (XXIV)

wherein $R^1$ is as defined for general formula (I);

and a copper (I) salt, particularly a copper (I) halide such as copper (I) iodide.

The reaction may be conducted in an organic solvent such as tetrahydrofuran, other ethers such as diethylether or a mixture thereof.

Alternatively, the addition can be carried out using Grignard reagents $R^1MgX$, where $R^1$ is as defined for general formula (I) and X is a halide, for example ethylmagnesium bromide and the reaction is suitably conducted in the presence of a zinc (II) salt such as zinc chloride and a catalytic amount of a copper (I) or copper(II) salt or complex, for example copper (I) chloride, copper (II) chloride or a copper(I) or copper (II) acetylacetonate (acac) complex.

The reaction may be carried out in an organic solvent, for example an ether such as THF, 2-methyl THF, methyl tert-butyl ether (tBME), diethyl ether. Surprisingly, the reaction temperature is not particularly significant and while in some cases the reaction may be carried out at reduced temperature, for example at about −25 to 0° C., it has also been successfully conducted at higher temperatures of up to about 55° C.

The process for preparing a compound of formula (I) from a compound of formula (II) is new and itself forms a part of the invention.

The method is particularly suitable for the preparation of compounds of general formula (I) in which $R^4$ is $C(O)OR^{10}$ from compounds of general formula (II) where $R^4$ is also $C(O)OR^{10}$, where $R^{10}$ is as defined above but is especially H, $C_{1-6}$ alkyl or benzyl.

Alternatively, compounds of formula (I) can be prepared from other compounds of general formula (I). For example, a compound of general formula (I) in which $R^4$ is $C(O)OR^{10}$ may be converted to a compound of general formula (I) in which $R^4$ is $C(O)NR^{10}R^{11}$, $S(O)R^{10}$, $SO_2R^{10}$, $OSO_2R^{10}$, $SO_3R^{10}$, or $OSO_3R^{10}$.

Compounds of general formula (I) in which $R^4$ is $SO_3R^{10}$ may be synthesised from compounds of general formula (I) in which $R^4$ is C(O)OH by the methods taught in WO2008/002573, WO2010/014836 and WO2014/066819.

Thus a compound of formula (I) in which $R^4$ is C(O)OH may be reacted with a $C_{1-6}$ alkanoyl or benzoyl chloride or with a $C_{1-6}$ alkanoic anhydride to protect the OH groups. The protected compound may then be reacted with a reducing agent such as a hydride, suitably lithium aluminium hydride or sodium borohydride in order to reduce the carboxylic acid group to OH. The alcohol group may be replaced by a halogen, for example bromine or iodine, using the triphenyl phosphine/imidazole/halogen method described by Classon et al, *J. Org. Chem.*, 1988, 53, 6126-6130. The halogenated compound may then be reacted with sodium sulphite in an alcoholic solvent to give a compound with a $SO_3^-Na^+$ substituent.

A compound of general formula (I) in which $R^4$ is $OSO_3R^{10}$ can be obtained by reacting the alcohol obtained from reducing the protected carboxylic acid as described above with chlorosulfuric acid in the presence of a base such as triethylamine to yield the protected triethylammonium salt. Protecting groups can be removed using base hydrolysis as described above. Reduction of the carboxylic acid followed by reaction of the resultant alcohol with chlorosulfurous acid yields a compound of general formula (I) in which $R^4$ is $OSO_2R^{10}$.

Compounds of general formula (I) in which $R^4$ is $C(O)NR^{10}R^{11}$ may be prepared from the carboxylic acid by reaction with an amine of formula H—$NR^{10}R^{11}$ in a suitable solvent with heating. Compounds of general formula (I) in which $R^4$ is $C(O)NR^{10}R^{11}$ or $OSO_3R^{10}$ may also be prepared by methods similar to those described by Festa et al, *J. Med. Chem.*, 2014, 57, 8477-8495.

Compounds of general formula (I) with other $R^4$ groups may be prepared from the above compounds of general formula (I) by methods which are familiar to those of skill in the art. These methods also form an aspect of the invention.

Compounds of general formula (II) may be prepared from compounds of formula (III):

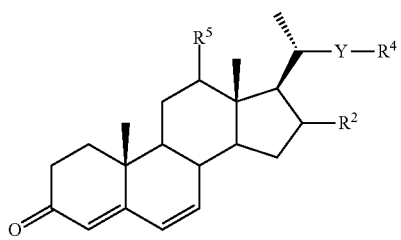

wherein $R^2$, $R^4$, $R^5$ and Y are as defined in general formula (I);

by oxidation, for example using bis(monoperoxyphthalate) hexahydrate (MMPP) or 3-Chloroperoxybenzoic acid, (mCPBA).

The reaction using MMPP may be carried out in an organic solvent such as ethyl acetate and if mCPBA is used, the reaction may be carried out in a solvent such as dichloromethane or toluene. Suitably, the reaction is conducted at or just below the reflux temperature of the solvent.

Compounds of general formula (III) may be prepared from compounds of general formula (IV):

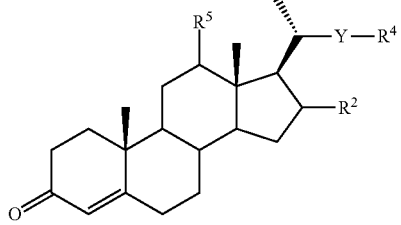

wherein $R^2$, $R^4$, $R^5$ and Y are as defined in general formula (I);

by reaction with an oxidizing agent such as chloranil.

The reaction may be carried out under acidic conditions, for example in the presence of acetic acid, and in an organic solvent such as toluene.

Some compounds of general formulae (II), (III) and (IV) are known and, for example Uekawa et al in *Biosci. Biotechnol. Biochem.*, 2004, 68, 1332-1337 describe the synthesis of (22E)-3-oxo-4,22-choladien-24-oic acid ethyl ester from stigmasterol followed by its conversion to (22E)-3-oxo-4,6,22-cholatrien-24-oic acid ethyl ester, which has the formula:

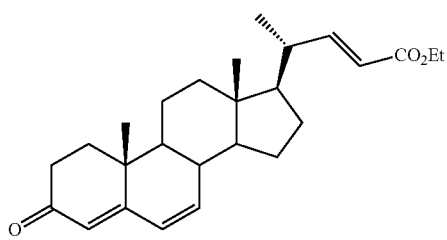 [SMILES: CCOC(=O)/C=C/[C@@H](C)[C@H]1CCC2C3C=CC4=CC(=O)CC[C@]4(C)C3CC[C@@]21C]

Uekawa et al then go on to describe the conversion of this compound to (6α, 7α, 22E)-6,7-epoxy-3-oxo-4,22-choladien-24-oic acid ethyl ester, a compound of general formula (II) in which $R^2$ and $R^5$ are H, Y is —CH=CH—, and $R^4$ is $C(O)OCH_2CH_3$.

Other compounds of general formulae (II), (III) and (IV) may be prepared by analogous methods from phytosterols similar to stigmasterol.

Stigmasterol and other phytosterols are plant sterols and are readily available or may be prepared by known routes.

Compounds of general formula (IV) may also be prepared from compounds of general formula (Va):

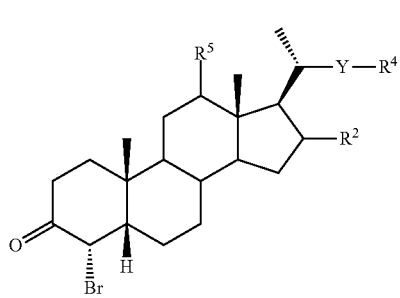

wherein $R^2$, $R^4$, $R^5$ and Y are as defined in general formula (I);

by reaction with lithium bromide and a base such as lithium carbonate. The reaction may be carried out in a solvent such as N,N-dimethylformamide (DMF) and at a temperature of about 120° C. to 180° C.

Compounds of general formula (Va) may be obtained by bromination of a compound of general formula (V):

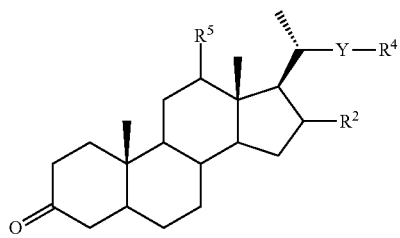

wherein $R^2$, $R^4$, $R^5$ and Y are as defined in general formula (I);

using, for example bromine in acetic acid.

Compounds of general formula (V) may be prepared from compounds of general formula (VI):

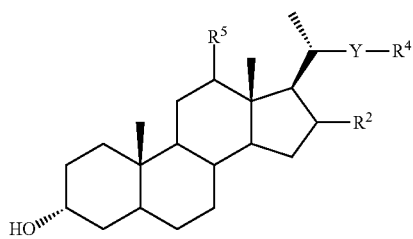

wherein $R^2$, $R^4$, $R^5$ and Y are as defined in general formula (I);

by oxidation, typically with a chromium-based oxidizing agent or with sodium hypochlorite.

Compounds of general formula (VI) in which $R^4$ is $C(O)OR^{10}$, where $R^{10}$ is $C_{1-6}$ alkyl or benzyl may be prepared from compounds of general formula (VI) in which $R^4$ is C(O)OH by esterification, typically by reaction with an appropriate alcohol under acidic conditions.

Compounds of general formula (VI) in which $R^4$ is C(O)OH and $R^5$ is H may be prepared from compounds of general formula (VII):

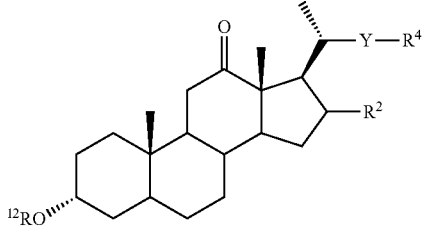

(VII)

wherein $R^2$ and Y are as defined in general formula (I);
$R^4$ is $C(O)OR^{10}$, where $R^{10}$ is $C_{1-6}$ alkyl or benzyl; and
$R^{12}$ is a protected OH;

by reaction with a reducing agent, typically hydrazine, under basic conditions and in an alcoholic or glycolic solvent, for example diethylene glycol.

Where $R^{12}$ is a protected OH group which is stable under basic conditions, the reaction may be followed by a reaction to remove the protecting group $R^{12}$ to leave an OH group.

Protecting groups for OH are discussed above and, for example, $R^{12}$ may be a group $C(O)R^{14}$, where $R^{14}$ is as defined above, in particular, $C_{1-6}$ alkyl or benzyl. Silyl ethers are also suitable, and in this case, $R^2$ and/or $R^5$ may independently be a group $Si(R^{16})_3$, where $R^{16}$ is as defined above but is especially $C_{1-6}$ alkyl or phenyl. Other suitable protecting groups for OH are well known to those of skill in the art (see Wuts, PGM and Greene, TW(2006) "Greene's Protective Groups in Organic Synthesis", 4$^{th}$ Edition, John Wiley & Sons, Inc., Hoboken, N.J., USA).

Particularly suitable $R^{12}$ groups include groups which are not stable in the presence of a base since this removes the need for the additional step of removing the protecting group. An example of a group $R^{12}$ which is not stable in basic conditions is a group $C(O)R^{14}$, where $R^{14}$ is as defined above, and is particularly $C_{1-6}$ alkyl or benzyl.

Alternatively, the reaction may be carried out in 2 steps such that the compound of general formula (VII) is reacted with a compound of general formula (XXXII):

$R^{20}$—NH—NH$_2$     (XXXII)

wherein $R^{20}$ is a leaving group such as toluene sulfonyl or methane sulfonyl;
to give a compound of general formula (XXXIII):

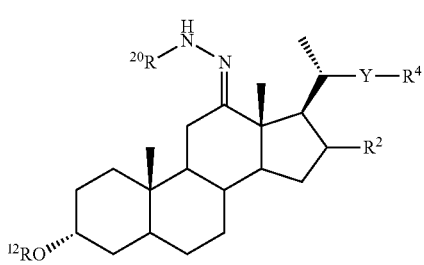

(XXXIII)

followed by reduction with a suitable reducing agent. Examples of reducing agents which can be used in this reaction include hydrides such as sodium borohydride, sodium cyanoborohydride, lithium aluminum hydride etc.

Compounds of general formula (VII) may be prepared from compounds of general formula (VIII):

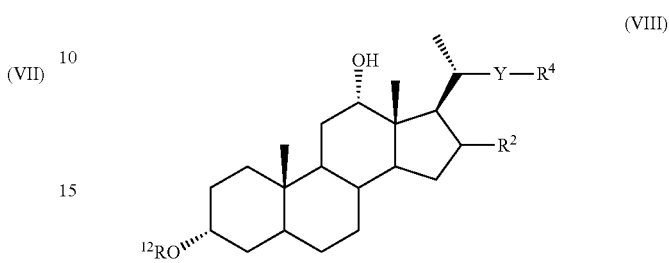

(VIII)

wherein $R^2$ and Y are as defined in general formula (I);
$R^4$ is $C(O)OR^{10}$, where $R^{10}$ is $C_{1-6}$ alkyl or benzyl; and
$R^{12}$ is as defined above, especially —$C(O)C_{1-6}$ alkyl;
by reaction with an oxidizing agent, for example sodium hypochlorite.

The reaction may be carried out under acidic conditions, for example in the presence of acetic acid, and in an organic solvent such as ethyl acetate.

Compounds of general formula (VIII) may be prepared from compounds of general formula (IX):

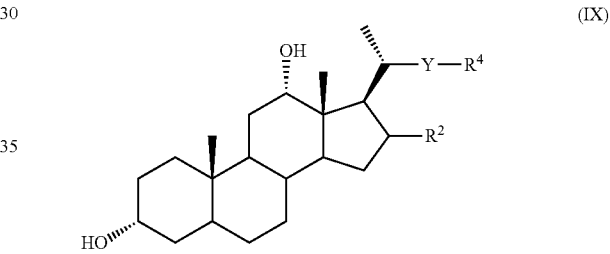

(IX)

wherein $R^2$ and Y are as defined in general formula (I);
$R^4$ is $C(O)OR^{10}$, where $R^{10}$ is $C_{1-6}$ alkyl or benzyl;
by reaction with an agent suitable to introduce the protecting group $R^{12}$. For example, when $R^{12}$ is $C(O)R^{14}$, the compound of general formula (IX) may be reacted with a carboxylic acid anhydride or an acid chloride in the presence of a weak base such as pyridine, suitably catalysed by 4-dimethylaminopyridine (DMAP). The reaction may be conducted in a solvent such as ethyl acetate.

Compounds of general formula (IX) may be prepared by the esterification of compounds of general formula (X):

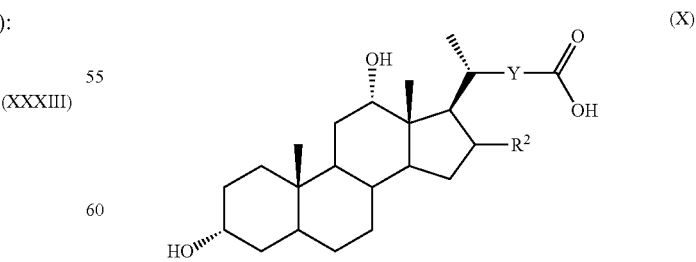

(X)

wherein $R^2$ and Y are as defined in general formula (I).

The reaction may be carried out by reacting the acid of general formula (X) with a suitable alcohol under acidic conditions.

Compounds of general formula (X) are known. For example, the compound of general formula (X) in which Y is —$CH_2CH_2$— and $R^2$ is H is deoxycholic acid, which is readily available from a number of sources.

Other bile acids with different values for Y and $R^2$ can be used as alternative starting materials.

An alternative route to compounds of general formula (IV) is as shown in Scheme 1 in which androstenedione is converted to a compound of general formula (IV) in which $R^2$ and $R^5$ are H; $R^4$ is —$C(O)OCH_3$ and Y is either —$CH_2CH_2$— or —CH=CH—.

wherein $R^2$ and $R^5$ are as defined for general formula (I); using a compound of general formula (XII):

(XII)

wherein $R^{10}$ is as defined for general formula (I).

Scheme 1

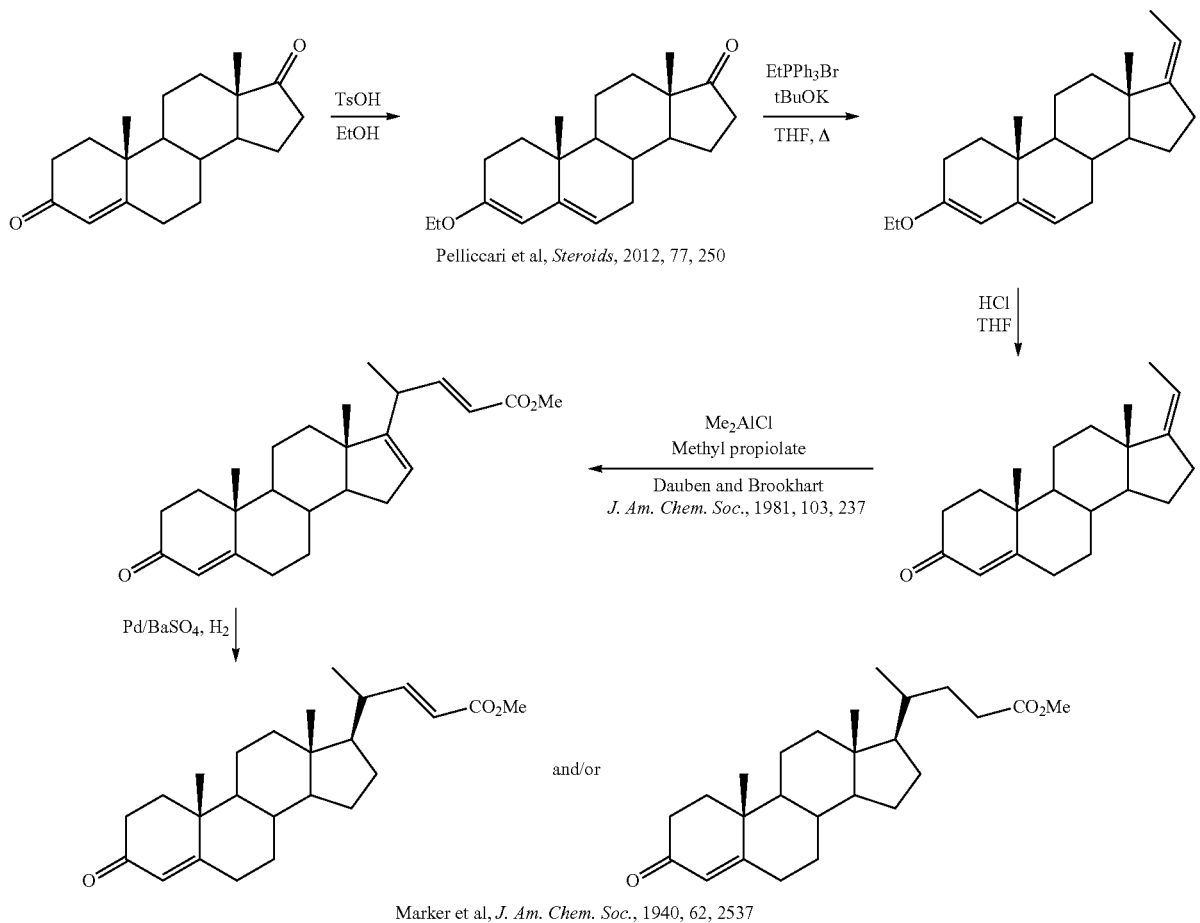

An alternative route to compounds of general formula (III) in which Y is an alkenylene group is by use of an olefination reaction, for example a Horner-Wadsworth-Emmons (HWE) olefination of a compound of general formula (XI):

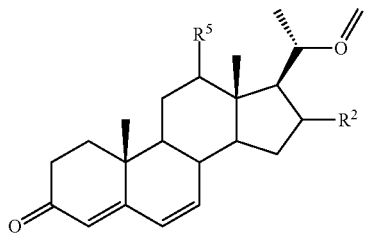

(XI)

The reaction may be carried out under standard HWE conditions, for example using a base such as sodium hydride.

Compounds of general formula (XII) are readily available or may be prepared by methods known to those of skill in the art.

Other olefination reactions, such as Tebbe olefination, Wittig reaction or a Julia-Kocienski olefination, would also give rise to compounds of general formula (III) in which Y is an alkenylene group. These olefination reactions are familiar to a chemist of skill in the art.

Compounds of general formula (XI) may be prepared by reaction of a compound of general formula (XIII) with ozone

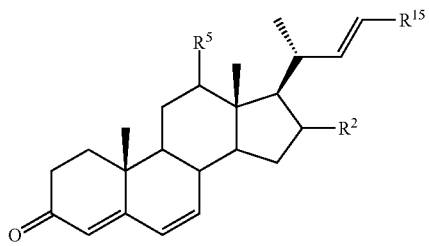

(XIII)

wherein $R^2$ and $R^5$ are as defined for general formula (I) and $R^{15}$ is $C_{1-6}$ alkyl.

An example of a reaction of this type is given in U.S. Pat. No. 2,624,748.

Compounds of general formula (XIII) may be prepared by reaction of a compound of general formula (XIV):

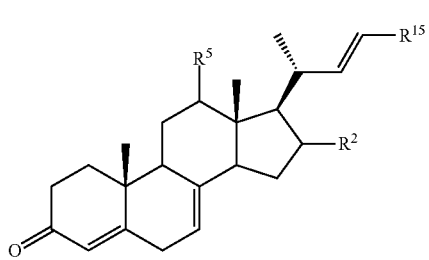

(XIV)

wherein $R^2$ and $R^5$ are as defined for general formula (I) and $R^{15}$ is $C_{1-6}$ alkyl with an acid in a solvent such as methanol.

Compounds of general formula (XIV) may be prepared by oxidation of a compound of general formula (XV):

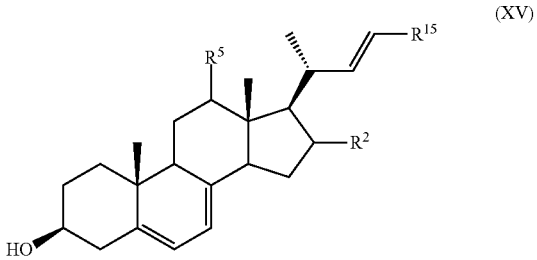

(XV)

wherein $R^2$ and $R^5$ are as defined for general formula (I) and $R^{15}$ is $C_{1-6}$ alkyl using an Oppenauer oxidation.

Examples of the conversion of compounds of general formula (XV) to compounds of general formula (XIII) are taught by Shepherd et al, *J. Am. Chem. Soc.* 1955, 77, 1212-1215 and Goldstein, *J. Med. Chem.* 1996, 39, 5092-5099.

One example of a compound of general formula (XV) is ergosterol, which is a fungal sterol and Scheme 2 below shows the conversion of ergosterol to a compound of general formula (III) in which both $R^2$ and $R^5$ are H, Y is CH=CH$_2$ and $R^4$ is C(O)OR$^{10}$, where $R^{10}$ is ethyl.

Scheme 2

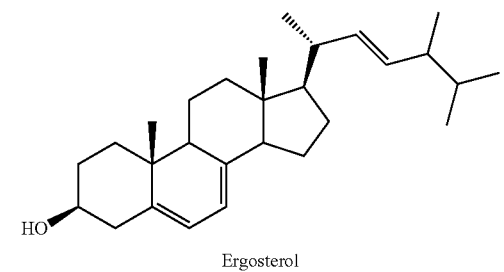

Ergosterol

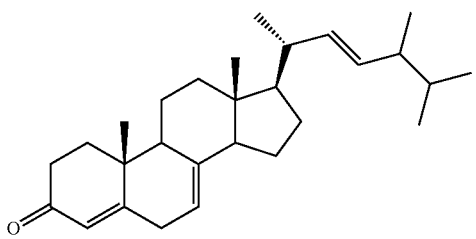

Goldstein et al
*J. Med. Chem.*, 1996, 39, 5092
Shepherd et al
*J. Am. Chem. Soc.*, 1955, 77, 1212 conc. HCl
MeOH

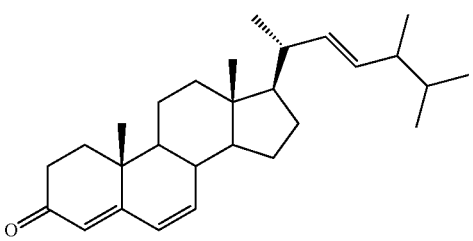

Ozone
Levin and McIntosh,
U.S. Pat. No. 2,624,748

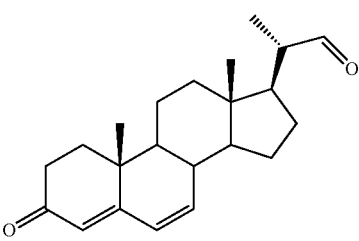

olefination

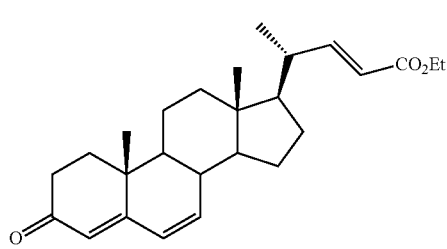

As with the compounds of general formula (I), compounds of general formulae (II) to (X), (Va) and (XXXIII) in which $R^4$ is $C(O)R^{10}$, $C(O)NR^{10}R^{11}$, $S(O)R^{10}$, $SO_3R^{10}$, or $OSO_3R^{10}$ may be prepared from the corresponding compounds in which $R^4$ is $C(O)OR^{10}$ by reaction with an appropriate reagents using methods well known to those of skill in the art. For example, the methods described in WO2008/002573 and WO2010/014836 or methods similar to those described by Classon et al, *J. Org. Chem.*, 1988, 53, 6126-6130 and Festa et al, *J. Med. Chem.*, 2014, 57, 8477-8495.

Compounds of general formula (I) are intermediates in the synthesis of compounds of general formula (XVIII):

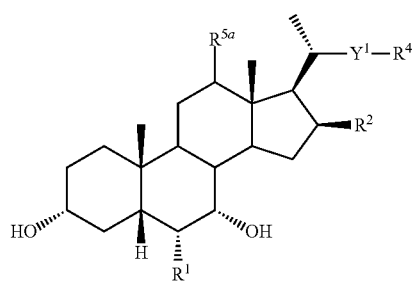

(XVIII)

wherein $R^1$ and $R^4$ are as defined in general formula (I);
$R^2$ is H, halo or OH;
$R^{5a}$ is H or OH; and
$Y^1$ is a bond or an alkylene linker group having from 1 to 20 carbon atoms and optionally substituted with one or more group $R^3$; wherein $R^3$ is as defined for general formula (I).

The compounds of general formula (I) may be converted to compounds of general formula (XVIII) in a 4 step process via intermediates of general formulae (XIX), (XX) and (XXI) as described below.

Therefore, in a further aspect of the invention there is provided a process for the preparation of a compound of general formula (XVIII), the process comprising:
i. reducing a compound of general formula (I) using a suitable reducing agent to give a compound of general formula (XIX):

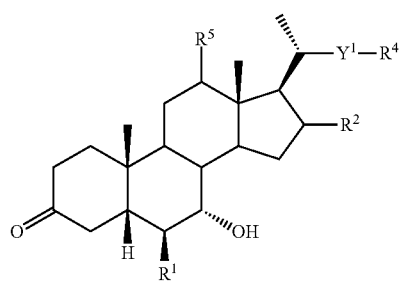

(XIX)

wherein $R^1$, $R^2$, $R^4$ and $R^5$ are as defined in general formula (I); and
$Y^1$ is as defined in general formula (XVIII);
ii. oxidising the compound of general formula (XIX) using a suitable oxidizing agent to give a compound of general formula (XX):

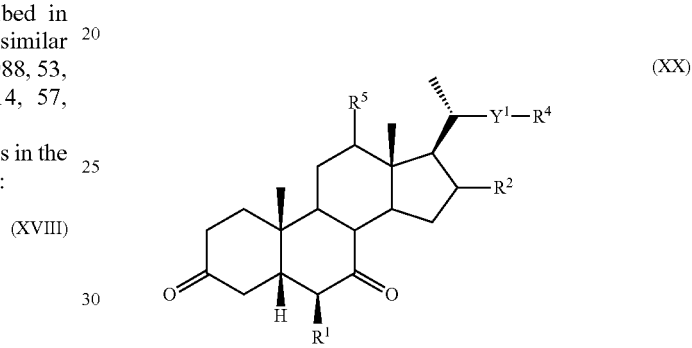

(XX)

wherein $R^1$, $R^2$, $R^4$ and $R^5$ are as defined in general formula (I); and
$Y^1$ is as defined in general formula (XVIII);
iii. epimerisation of the compound of general formula (XX) to give a compound of general formula (XXI):

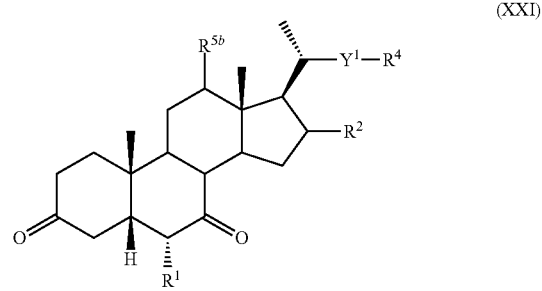

(XXI)

wherein $R^1$ and $R^4$ are as defined in general formula (I);
$Y^1$ is as defined in general formula (XVIII);
$R^2$ is H, halo or OH or a protected OH group which is stable under basic conditions; and
$R^{5b}$ is H or OH or a protected OH group which is stable under basic conditions; and
(iv) reduction of the compound of general formula (XXI) using a suitable reducing agent and, where $R^2$ and/or $R^{5b}$ is a protected OH, removal of the protecting group(s), to give a compound of general formula (XVIII) as defined above, wherein removal of the protecting group can take place before or after the reduction; and optionally
(v) conversion of a compound of general formula (XVIII) to another compound of general formula (XVIII).

Compounds of general formula (XVIII) are potent agonists of FXR and TGR5 and include obeticholic acid, which is a compound of formula (XVIII) in which $R^1$ is ethyl, $R^2$ and $R^{5a}$ are both H, $Y^1$ is —$CH_2CH_2$—, and $R^4$ is C(O)OH.

In the compounds of general formulae (XVIII) to (XXI), more suitable values for $R^1$ and $R^4$ are as defined for general formula (I).

In some compounds of general formulae (XVIII) to (XXI), $Y^1$ is a bond.

In other compounds of general formulae (XVIII) to (XXI), $Y^1$ is an alkylene linker group having from 1 to 15 carbon atoms, more suitably 1 to 12, 1 to 10 or 1 to 8 carbon atoms and optionally substituted with one or more groups $R^3$ as defined above. Typically each $R^3$ is independently halo, $OR^8$ or $NR^8R^9$; where each of $R^8$ and $R^9$ is independently selected from H, methyl or ethyl, especially H or methyl.

In some suitable compounds of general formulae (XVIII) to (XXI), $Y^1$ is an unsubstituted alkylene or alkenylene linker having from 1 to 15 carbon atoms, more suitably 1 to 12, 1 to 10 or 1 to 8 carbon atoms.

In step (i) above, the conversion of the compound of general formula (I) to the compound of general formula (XIX) may be carried out by hydrogenation, usually catalytic hydrogenation. Suitable catalysts for the catalytic hydrogenation include a palladium/carbon, palladium/calcium carbonate, palladium/aluminium oxide, platinum/palladium or Raney nickel catalyst. The reaction may be carried out in an organic solvent, which may be an alcoholic solvent such as methanol, ethanol or isopropanol; ethyl acetate; pyridine; acetic acid; cyclopentyl methyl ether (CPME) or N,N-dimethylformamide (DMF). The organic solvent may optionally be mixed with a co-solvent such as acetone or water and/or a base such as triethylamine may also be added.

The choice of catalyst and solvent affects the ratio of the required product of general formula (XIX):

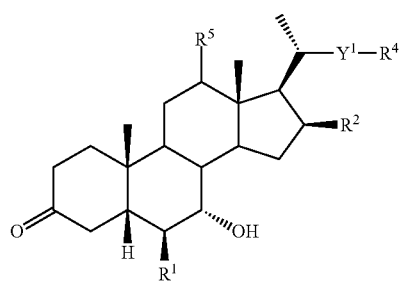

(XIX)

to its isomer of general formula (XXX):

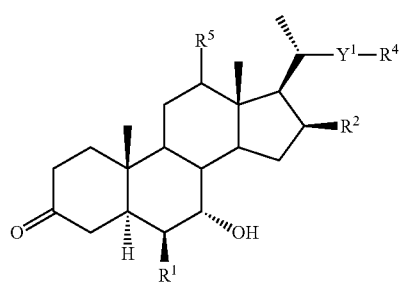

(XXX)

It also affects the rate of conversion of the intermediate of formula (XXXI):

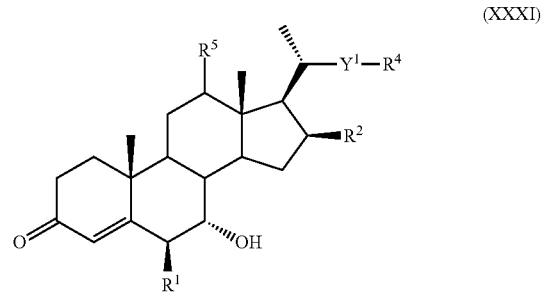

(XXXI)

to the product.

More suitably, a palladium/carbon or palladium/calcium carbonate catalyst is used. Typically, in the catalyst the palladium is present in an amount of 5-10% by weight with respect to the weight of the matrix (where the matrix is the carbon, calcium carbonate etc).

Solvents which give superior ratios of (XIX): (XXX) include methanol, ethanol and DMF, particularly methanol and DMF.

When methanol is used as the solvent, it may be used alone or in the presence of a base such as triethylamine. Suitably, the amount of triethylamine used is a substoichiometric amount, typically 0.1 to 0.5 equivalents with respect to the amount of starting material of general formula (I).

Methanol in the presence of triethylamine gave a particularly high ratio of the required product of general formula (XIX) to isomer of general formula (XXX).

Reactions conducted with methanol as the solvent may be carried out at a temperature of about −30 to 25° C. and the temperature has little effect on the ratio of (XIX): (XXX).

When DMF is used as a solvent, it may be mixed with a co-solvent such as acetone, TBME, THF, acetonitrile or acetone/water. Optionally, the solvent contains a base such as triethylamine in a substoichiometric amount, typically 0.1 to 0.5 equivalents with respect to the amount of starting material of general formula (I).

Reactions conducted using DMF as solvent appear to be more sensitive to temperature than reactions carried out in methanol and the ratio of (XIX):(XXX) decreases with increasing temperature. Suitably, therefore the reaction is conducted at a temperature of −30 to 0° C., more suitably −20 to −10° C.

It has been found that the pressure of hydrogen has little effect on the selectivity and therefore the hydrogen pressure is suitably about 1 atmosphere.

Similarly dilution does not appear to have a major impact on the selectivity and therefore the solvent may be used in any convenient amount.

Hydrogenation of a compound of formula (I) will also reduce any alkene bonds, if present, in the linker Y.

In step (ii) of the process set out above, the oxidation reaction may be carried out using any suitable method. One suitable method is a Dess-Martin periodinane (1,1,1-triacetoxy-1,1-dihydro-1,2-benziodoxol) oxidation, which may be carried out in a chlorinated solvent such as chloroform or dichloromethane at a temperature of about 15 to 25° C., suitably at room temperature.

An alternative oxidation method is oxidation using a hypochlorite, for example sodium hypochlorite, under acidic conditions, for example provided by acetic acid. The reaction may be carried out in an aqueous solvent and at a temperature of 0 to 15° C., more usually at about 0 to 10° C.

Other oxidation methods include a Jones reaction using sodium dichromate or, more usually, chromic trioxide in dilute sulfuric acid. This process is known to be reliable for the clean conversion of bile acid hydroxyl groups to the corresponding keto derivatives (Bortolini et al, *J. Org. Chem.*, 2002, 67, 5802). Alternatively oxidation may be carried out using TEMPO ((2,2,6,6-Tetramethyl-piperidin-1-yl)oxy) or a derivative thereof.

The epimerisation reaction of step (iii), suitably comprises treating the compound of general formula (XX) with a base. The compound of general formula (XX) may be dissolved in an alcoholic solvent, optionally mixed with water and contacted with a base, for example sodium or potassium hydroxide or a sodium or potassium alkoxide, typically an ethoxide.

In the case of compounds of general formula (XX) in which $R^4$ is $C(O)OR^{10}$, where $R^{10}$ is $C_{1-6}$ alkyl or benzyl and where a strong base such as sodium or potassium hydroxide is used, the epimerization reaction of step (iii) may be accompanied by hydrolysis to give a compound of general formula (XXI) in which $R^4$ is C(O)OH.

If, in the compound of general formula (XX), $R^2$ and/or $R^5$ is a protected OH, for example a group $OC(O)OR^{14}$, where $R^{14}$ is as defined above but is especially $C_{1-6}$ alkyl or benzyl, this will be removed during the epimerisation step to give a compound of general formula (XXI) in which $R^2$ and/or $R^{5b}$ is OH. Other protected OH groups which are stable in basic conditions (for example a group $OSi(R^{16})_3$ where each $R^{16}$ is independently as defined above but is especially $C_{1-6}$ alkyl or phenyl) may be removed before or after step (iv).

In step (iv), the reducing agent is typically a hydride, such as sodium borohydride which may be used in a solvent such as a mixture of tetrahydrofuran and water. Typically, this reaction is carried out under basic conditions, for example in the presence of a strong base such as sodium or potassium hydroxide and at a temperature of about 0 to 110° C., more usually 60 to 100° C. A compound of general formula (XVIII) in which $R^4$ is C(O)OH may be produced by the reduction of a compound of general formula (XXI) in which $R^4$ is C(O)OH.

Compounds of general formulae (XVIII) to (XXI) in which $R^4$ is $C(O)R^{10}$, $C(O)NR^{10}R^{11}$, $S(O)R^{10}$, $SO_2R^{10}$, or $OSO_2R^{10}$ may be prepared from the corresponding compounds in which $R^4$ is $C(O)OR^{10}$ by reaction with an appropriate reagents using methods well known to those of skill in the art.

Compounds of general formulae (XVIII) to (XXI) in which $R^4$ is $SO_3R^{10}$ may be synthesised from compounds of general formulae (XVIII) to (XXI) in which $R^4$ is C(O)OH by the methods taught in WO2008/002573, WO2010/014836 and WO2014/066819.

Thus a compound of formula (I) in which $R^4$ is C(O)OH may be reacted with a $C_{1-6}$ alkanoyl or benzoyl chloride or with a $C_{1-6}$ alkanoic anhydride to protect the OH groups. The protected compound may then be reacted with a reducing agent such as a hydride, suitably sodium borohydride in order to reduce the carboxylic acid group to OH. The alcohol group may be replaced by a halogen, for example bromine or iodine, using the triphenyl phosphine/imidazole/halogen method described by Classon et al, *J. Org. Chem.*, 1988, 53, 6126-6130. The halogenated compound may then be reacted with sodium sulphite in an alcoholic solvent to give a compound with a $SO_3^-Na^+$ substituent.

Compounds of general formulae (XVIII) to (XXI) in which $R^4$ is $OSO_3R^{10}$ can be obtained by reacting the alcohol obtained from reducing the protected carboxylic acid with chlorosulfuric acid in the presence of a base such as triethylamine to yield the protected triethylammonium salt. Protecting groups can be removed using base hydrolysis as described above. Reduction of the carboxylic acid followed by reaction of the resultant alcohol with chlorosulfurous acid yields a compound of general formulae (XVIII) to (XXI) in which $R^4$ is $OSO_2R^{10}$.

Compounds of general formulae (XVIII) to (XXI) in which $R^4$ is $C(O)NR^{10}R^{11}$ may be prepared from the carboxylic acid by reaction with an amine of formula H—$NR^{10}R^{11}$ in a suitable solvent with heating. Compounds of general formulae (XVIII) to (XXI) in which $R^4$ is $C(O)NR^{10}R^{11}$ or $OSO_3R^{10}$ may also be prepared by methods similar to those described by Festa et al, *J. Med. Chem.*, 2014, 57 (20), 8477-8495. These methods also form an aspect of the invention.

A compound of general formula (XVIII) to (XXI) in which $R^4$ is $C(O)R^{10}$ can be obtained by reduction of a compound in which $R^4$ is $C(O)OR^{10}$ using one equivalent of diisobutyl aluminium hydride (DIBAL) to obtain an aldehyde in which $R^4$ is C(O)H (see, for example, WO2011/014661).

Alternatively, the aldehyde may be prepared by oxidation of a protected compound in which $R^4$ is OH prepared as described above. The oxidation may be Swern oxidation carried out using oxalyl chloride and dimethyl sulfoxide followed by triethylamine (see, for example Xiang-Dong Zhou et al, *Tetrahedron*, 2002, 58, 10293-10299). Alternatively, the oxidation may be carried out using an oxidating agent such as pyridinium chlorochromate (PCC) as described by Carnell et al (*J. Med. Chem.*, 2007, 50, 2700-2707).

A compound of general formula (I) in which $R^4$ is $C(O)R^{10}$ where $R^{10}$ is other than hydrogen can be obtained by known methods, for example by the reaction of the aldehyde in which $R^4$ is C(O)H with a suitable Grignard reagent, followed by oxidation. Such methods are well known to those of skill in the art.

Figure 1:
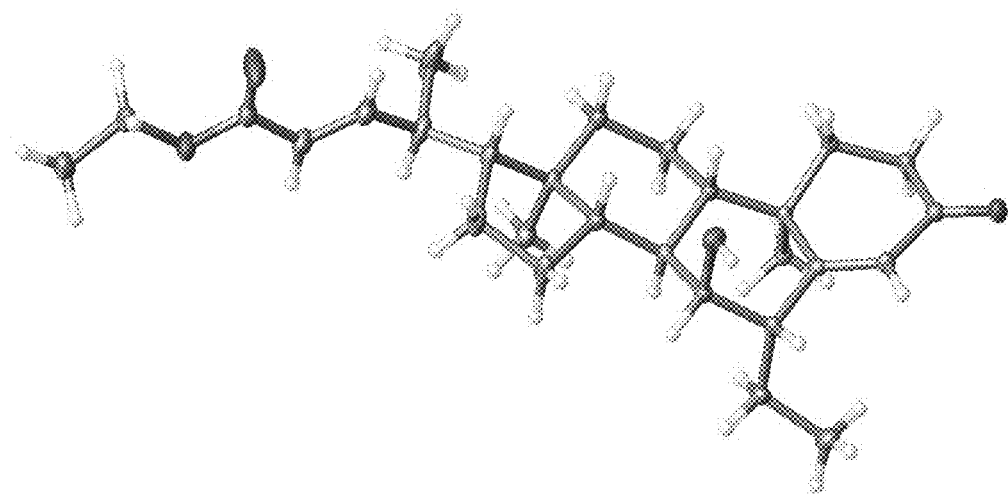
FIG. 1 is an image showing the chemical structure of (6β, 7α, 22E)-6-ethyl-7-hydroxy-3-oxo-4,22-choladien-24-oic acid ethyl ester.

The invention will now be described in greater detail with reference to the examples.

In the examples, the following abbreviations were used:
AcOH Acetic acid
CPME Cyclopentyl methyl ether
DMF N,N-dimethylformamide
EtOAc Ethyl acetate
EtOH Ethanol
IPA Isopropyl alcohol
MeOH Methanol
NEt₃ Triethylamine
nBuOAc n-butyl acetate
TBME t-butyl methyl ether
THF Tetrahydrofuran
TLC Thin layer chromatography

EXAMPLES 1 TO 4

Synthesis of (6β, 5β, 7α)-6-ethyl-7-hydroxy-3-oxo-cholan-24-oic acid ethyl ester from Stigmasterol

EXAMPLE 1

Synthesis of (22E)-3-oxo-4,6,22-cholatrien-24-oic acid ethyl ester

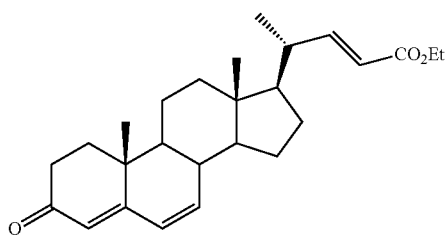 [SMILES: CCOC(=O)/C=C/[C@@H](C)[C@H]1CCC2C3C=CC4=CC(=O)CC[C@]4(C)C3CC[C@@]21C]

The starting material, (22E)-3-oxo-4,22-choladien-24-oic acid ethyl ester, was prepared from stigmasterol according to the method described by Uekawa et al in *Biosci, Biotechnol, Biochem.*, 2004, 68, 1332-1337.

(22E)-3-oxo-4,22-choladien-24-oic acid ethyl ester (1.00 kg, 2.509 mol; 1 eq) was charged to a reaction vessel, followed by AcOH (3 vol, 3.0 L) and toluene (1 vol, 1.0 L) with stirring. Chloranil (0.68 kg, 2.766 mol; 1.1 eq) was then charged and the reaction mixture heated to 100° C. and maintained at this temperature for 1-2 h (IPC by TLC on silica, eluent 3:7 EtOAc:Heptane; Starting Material: $R_f$ 0.50, Product: $R_f$ 0.46; visualise with anisaldehyde stain). The mixture was then cooled in an ice/water bath to 10° C. and the resulting solid was filtered off. The filter-cake was washed with premixed 3:1 AcOH:Toluene (4×0.5 vol) at 5° C.±4° C. and the filtrate concentrated in vacuo at up to 70° C. The residue was dissolved in acetone (3 vol), then 3% w/w aq. NaOH (10 vol) was charged dropwise with stirring, maintaining the temperature below 30° C. (exothermic). The resulting suspension was cooled to 10-15° C. and stirred for 30 mins. The solids were collected by filtration and the filter cake was washed with premixed 1:1 acetone:water (1×2 vol then 3×1 vol). The filter cake (tan solid) was dried under vacuum at 70-75° C., 672 g (68% yield). Characterisation of the compound agrees with the data published in the literature.

EXAMPLE 2

(6α, 7α, 22E)-6,7-epoxy-3-oxo-4,22-choladien-24-oic acid ethyl ester

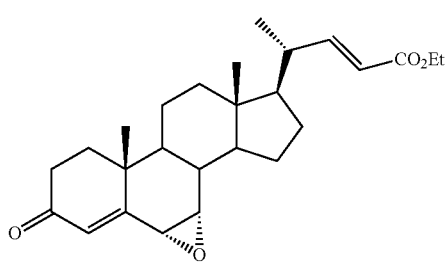 [SMILES: CCOC(=O)/C=C/[C@@H](C)[C@H]1CCC2C3C(CC[C@@]21C)[C@@]1(C)CCC(=O)C=C1[C@H]1O[C@@H]31]

To a solution of (22E)-3-oxo-4,6,22-cholatrien-24-oic acid ethyl ester (58.0 g, 146.3 mmol) in EtOAc (1.0 L) at reflux was added 80% MMPP (magnesium bis(monoperoxyphthalate) hexahydrate, 197.0 g, ca. 318.6 mmol) in four equal portions at 30 min intervals. The suspension was vigorously stirred at reflux for 5 h and at ambient temperature for a further 16 h. The reaction was then heated to reflux and stirred for an additional 6 h. The mixture was cooled to ca. 50° C. and the solids were filtered and rinsed with hot EtOAc (200 mL). The filtrate was subsequently washed with 20% aq. NaHSO$_3$ (100 mL), 1M aq. NaOH (100 mL then 200 mL) and 10% aq. NaCl (250 mL), dried over Na$_2$SO$_4$, filtered and concentrated in vacuo. The residue (yellow solid) was crystallised from minimum volume of EtOAc at 60° C. to give the epoxide product as off white/pale yellow crystals (25.7 g, 43% yield, prisms). Characterisation of the compound agrees with the data published in the literature.

EXAMPLE 3

Synthesis of (6β, 7α, 22E)-6-ethyl-7-hydroxy-3-oxo-4,22-choladien-24-oic acid ethyl ester

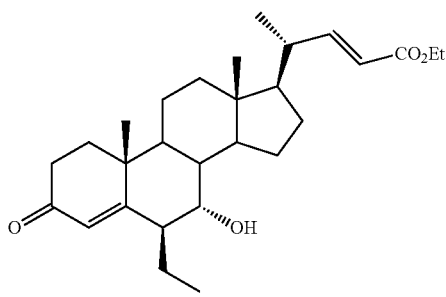 [SMILES: CCOC(=O)/C=C/[C@@H](C)[C@H]1CCC2C3C(CC[C@@]21C)[C@@]1(C)CCC(=O)C=C1[C@H](CC)[C@H]3O]

Method 1:

To a suspension of CuI (1.40 g, 7.35 mmol) in diethyl ether (10 mL), cooled to −78° C. under an argon blanket was charged EtLi (28.8 mL, 14.4 mmol, 0.5 M solution in benzene/cyclohexane). The thick white suspension formed was allowed to warm to 020 C., stirred for 5 mins (forming a dark solution) and cooled to −78° C. A solution of (6α, 7α, 22E)-6,7-epoxy-3-oxo-4,22-choladien-24-oic acid ethyl ester (1.00 g, 2.42 mmol) in diethyl ether/THF (24 mL, 3:1) was prepared and charged to the vessel containing the organocuprate. THF (1 mL) was used to rinse the vessel that contained the solution of the epoxide and this was also charged to the organocuprate. The reaction mixture was allowed to warm to −4° C. over 30 mins after which time the reaction was complete by TLC (silica, 1:1 EtOAc:heptane). After a further 30 mins of stirring at c.a. −4° C. a solution of aq. sat. NH$_4$Cl was charged and the mixture was stirred over 30 mins. The mixture was transferred to a separating funnel and the aqueous phase was removed, along with solid material present at the interface. The organic phase was washed with 5 wt % aq NaHCO$_3$ (2×50 mL) and water (1×50 mL). TBME (50 mL) was used to extract the original aqueous phase from the reaction and the combined washes. The combined organic phases were concentrated and the residue was purified by chromatography using silica (25 g) as the stationary phase (gradient elution with 0-30% EtOAc in heptane) to give (6β, 7α, 22E)-6-ethyl-7-hydroxy-3-oxo-4,22-choladien-24-oic acid ethyl ester (0.63 g, 59%) (FIG. 1).

¹H NMR (400 MHz, CDCl₃): δ=6.82 (1H, dd, J=15.6, 8.9, C22H), 5.75 (1H, s, C4H), 5.74 (1H, d, J=15.6, C23H), 4.17 (2H, q, J=7.1, OCH$_2$CH$_3$), 3.72 (1H, br s, C7H), 2.52-2.25 (5H, m), 2.05-1.98 (2H, m), 1.82-1.10 (23H, m), 0.91 (3H, t, J=7.4, CH$_3$), 0.77 (3H, s, CH$_3$). ¹³C NMR (100 MHz, CDCl₃): δ=199.2, 171.2, 167.1, 154.5, 128.4, 119.0, 71.9, 60.1, 55.3, 54.9, 49.9, 44.3, 42.7, 39.6, 39.1, 38.3, 37.4, 35.6, 34.0, 28.0, 26.3, 23.6, 20.8, 19.7, 19.2, 14.2, 12.8, 12.0; (IR) $v_{max}$(cm$^{-1}$): 3467, 2939, 2870, 1716, 1651, 1457, 1268, 1229, 1034; HRMS (ESI-TOF) m/z: (M+H)⁺ calcd for C$_{28}$H$_{43}$O$_4$ 443.3161; found: 443.3156. mp=59.4-62.9° C.

Method 2

ZnCl₂ (32.84 g, 240.9 mmol) was dried under vacuum with slow stirring at 180° C. for 2 h. The flask was cooled to room temperature under an argon atmosphere and the residue was dissolved in THF (520 mL) and transferred via cannula into a three neck reaction flask equipped with mechanical stirrer and temperature probe. The solution was cooled in an ice bath to 0-3° C. and a 3M solution of EtMgBr in Et₂O (80 mL, 240.0 mmol) was added dropwise over 20 mins, maintaining the internal temperature below 10° C. Formation of a white precipitate (active zincate species) was observed after addition of ca. ⅓ of the Grignard solution. The mixture was stirred for 1.2 h at 0° C. before a solution of the epoxide (6α, 7α, 22E)-6,7-epoxy-3-oxo-4,22-choladien-24-oic acid ethyl ester (43.0 g, 104.2 mmol) in THF (300 mL) was added dropwise, maintaining the internal temperature below 10° C. Solid CuCl (1.03 g, 0.104 mmol) was then added in two equal portions with vigorous stirring. After 10 mins the cooling bath was removed and stirring continued at ambient temperature for an additional 1.2 h. The reaction was quenched by dropwise addition of sat. aq. NH₄Cl (800 mL) at <15° C. and stirred for 0.5 h. The mixture was filtered and the solid rinsed with TBME (150 mL). The phases were separated and the aqueous phase extracted with TBME 2×250 mL. The combined organic extracts were washed with 10% aq. NaCl (2×200 mL), dried over Na₂SO₄, filtered and concentrated in vacuo to give 43.7 g of the crude (6β, 7α, 22E)-6-ethyl-7-hydroxy-3-oxo-4,22-choladien-24-oic acid ethyl ester as a yellow foam.

Method 3

To a solution of ZnCl₂ in THF (0.5 M, 8.7 mL, 4.85 mmol, 0.9 eq) was charged anhydrous THF (8.0 mL) and the contents then cooled to −25° C. A solution of EtMgBr in TBME (1.0 M, 8.7 mL, 8.70 mmol, 1.8 eq) was added over 30 mins and the mixture stirred for 45 mins at −25° C. Solid CuCl (24 mg, 0.49 mmol, 0.05 eq) was added in one portion and a solution of (6α, 7α, 22E)-6,7-epoxy-3-oxo-4,22-choladien-24-oic acid ethyl ester (2.0 g, 4.85 mmol) in THF (8.0 mL) was added dropwise over 30 mins. The remaining solid CuCl (24 mg, 0.49 mmol, 0.05 eq) was added half way through the addition of (6α, 7α, 22E)-6,7-epoxy-3-oxo-4,22-choladien-24-oic acid ethyl ester. The reaction was stirred for 1 h at −25° C., (TLC 1:1 Heptane:EtOAc, visualised by UV and developed using Ceric Ammonium Molybdate stain) and then additional of EtMgBr in TBME (1.0 M, 2.9 mL, 2.91 mmol, 0.6 eq) was added over 10 mins. The reaction was stirred for 0.5 h at −25° C. and then quenched by the addition of sat. aq. NH₄Cl (5 mL), maintaining the temperature below −5° C. The inorganic salts were filtered off, rinsed with TBME and the filtrate phases were separated. The aqueous layer extracted with TBME and the combined organic extracts were washed with sat. aq. NH₄Cl (3×5 mL) and 10% brine (3×6 mL). The organic phase was concentrated in vacuo at 40° C. to give crude (6β, 7α, 22E)-6-ethyl-7-hydroxy-3-oxo-4,22-choladien-24-oic acid ethyl ester as a yellow foam (1.91 g).

Method 4

To a solution of ZnCl₂ in THF (0.5 M, 8.7 mL, 4.85 mmol, 0.9 eq) was charged anhydrous THF (8.0 mL) and the contents then heated to 40° C. A solution of EtMgBr in TBME (1.0 M, 8.7 mL, 8.70 mmol, 1.8 eq) was added over 30 mins and the mixture stirred for 45 mins at 40° C. Solid CuCl (24 mg, 0.49 mmol, 0.05 eq) was added in one portion and a solution of (6α, 7α, 22E)-6,7-epoxy-3-oxo-4,22-choladien-24-oic acid ethyl ester (2.0 g, 4.85 mmol) in THF (8.0 mL) was added dropwise over 30 mins. The remaining solid CuCl (24 mg, 0.49 mmol, 0.05 eq) was added half way through the addition of (6α, 7α, 22E)-6,7-epoxy-3-oxo-4,22-choladien-24-oic acid ethyl ester. The reaction was stirred for 1 h at 40° C., (TLC 1:1 Heptane:EtOAc, visualised by UV and developed using Ceric Ammonium Molybdate stain) and then quenched by the dropwise addition of sat. aq. NH₄Cl (5 mL). The inorganic salts were filtered off, rinsed with TBME and the filtrate phases were separated. The aqueous layer was extracted with TBME and then the combined organic extracts were washed with sat. aq. NH₄Cl (3×5 mL) and 10% brine (3×6 mL). The organic phase was concentrated in vacuo at 40° C. to give crude (6β, 7α, 22 E)-6-ethyl-7-hydroxy-3-oxo-4,22-choladien-24-oic acid ethyl ester as a yellow foam (2.08 g).

Method 5

To a solution of ZnCl₂ in THF (0.5 M, 8.7 mL, 4.85 mmol, 0.9 eq) was charged anhydrous THF (8.0 mL) and the contents then cooled to −15° C. A solution of EtMgBr in THF (1.0 M, 8.7 mL, 8.70 mmol, 1.8 eq) was added over 30 mins and the mixture stirred for 45 mins at −15° C. Solid CuCl (24 mg, 0.49 mmol, 0.05 eq) was added in one portion and a solution of (6α, 7α, 22E)-6,7-epoxy-3-oxo-4,22-choladien-24-oic acid ethyl ester (2.0 g, 4.85 mmol) in THF (8.0 mL) was added dropwise over 30 mins. The remaining solid CuCl (24 mg, 0.49 mmol, 0.05 eq) was added half way through the addition of (6α, 7α,22E)-6,7-epoxy-3-oxo-4,22-choladien-24-oic acid ethyl ester. The reaction stirred for 1 h at −15° C., (TLC 1:1 Heptane:EtOAc, visualised by UV and developed using Ceric Ammonium Molybdate stain) and then additional EtMgBr in THF (1.0 M, 4.35 mL, 4.36 mmol, 0.9 eq) was added over 15 mins and then quenched by the dropwise addition of sat. aq. NH₄Cl (5 mL). The inorganic salts were filtered off, rinsed with TBME and the filtrate phases were separated. The aqueous phase was extracted with TBME and then the combined organic extracts were washed with sat. aq. NH₄Cl (3×5 mL) and 10% brine (3×6 mL). The organic phase was concentrated in vacuo at 40° C. to give crude (6β, 7α, 22E)-6-ethyl-7-hydroxy-3-oxo-4,22-choladien-24-oic acid ethyl ester as a yellow foam (1.94 g).

EXAMPLE 4

Synthesis of (6β, 5β, 7α)-6-ethyl-7-hydroxy-3-oxo-cholan-24-oic acid ethyl ester

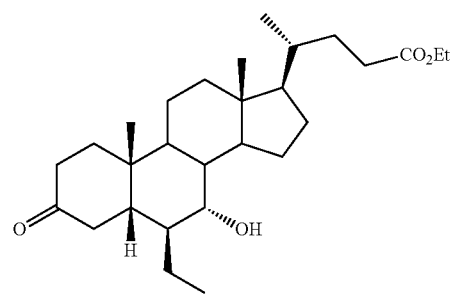 [SMILES: CCOC(=O)CC[C@@H](C)[C@H]1CCC2C3C(CC[C@@]21C)[C@@]1(C)CCC(=O)C[C@H]1[C@H](CC)[C@H]3O]

Method 1

To a suspension of 10 wt. % Pd/C (50% wet, 20 mg, 8.6 mol %) in DMF (2 mL) was added a solution of (6β, 7α, 22E)-6-ethyl-7-hydroxy-3-oxo-4,22-choladien-24-oic acid ethyl ester (50 mg, 0.11 mmol) in DMF (3 mL) and the reaction mixture was cooled to 0° C. The flask was evacuated then filled with hydrogen three times with vigorous stirring. After 3 h the flask was evacuated then filled with argon and the mixture filtered via syringe filter. The mixture was partitioned between TBME (30 mL) and $H_2O$ (20 mL). The organic phase was dried ($Na_2SO_4$) and concentrated in vacuo. The crude product (50 mg) was a 14:1 mixture of 5β to 5α isomers (analysed by $^1H$ NMR) of (6β, 5β, 7α)-6-ethyl-7-hydroxy-3-oxo-cholan-24-oic acid ethyl ester, yield 92%.

$^1H$ NMR (700 MHz, $CDCl_3$): δ=4.12 (2H, q, J=7.1, $OCH_2CH_3$), 3.71 (1H, br s, C7H), 3.34 (1H, dd, J=15.5, 13.6, C4H), 2.39-2.32 (2H, m), 2.24-2.20 (1H, m), 2.14-2.09 (2H, m), 2.03-1.91 (4H, m), 1.83-1.79 (2H, m), 1.68-1.63 (2H, m), 1.58 (1H, s), 1.55-1.12 (19H, m), 1.04 (3H, s), 0.95-0.93 (6H, m), 0.88 (1H, J=7.0), 0.71 (3H, s). $^{13}C$ NMR (100 MHz, $CDCl_3$): δ=213.5, 174.2, 72.1, 60.2, 55.9, 50.2, 49.8, 47.0, 46.7, 42.7, 39.5, 37.7, 36.3, 36.0, 35.7, 35.3, 34.2, 31.3, 31.0, 28.1, 27.7, 24.4, 23.8, 20.8, 18.3, 14.2, 13.9, 11.8. (IR) $v_{max}(cm^{-1})$: 3514, 2939, 2870, 1710, 1462, 1377, 1159, 1099, 1032; HRMS (ESI-TOF) m/z: $(M-H_2O+H)^+$ calcd for $C_{28}H_{45}O_3$ 429.3369; found: 429.3363.

Method 2

(6β, 7α, 22E)-6-ethyl-7-hydroxy-3-oxo-4,22-choladien-24-oic acid ethyl ester (20.0 g) was dissolved in DMF (400 mL) and added under argon to solid 10 wt. % Pd/C (50% wet, 10.0 g). The mixture was cooled in an ice-salt bath to approximately −15° C. and the flask was evacuated then filled with hydrogen three times with vigorous stirring. The mixture was stirred under an atmosphere of hydrogen for 6 h then the flask was evacuated, filled with argon and filtered through a pad of celite. The catalyst was rinsed with 400 mL of TBME. The filtrate was washed with 10% aq. NaCl (400 mL) and the aqueous phase extracted with TBME (400 mL). The combined organic phases were washed with 10% aq. NaCl (3×200 mL), dried over $Na_2SO_4$, filtered and concentrated in vacuo to give crude (6β, 5β, 7α)-6-ethyl-7-hydroxy-3-oxo-cholan-24-oic acid ethyl ester (20.0 g, ca. 28:1 5Hβ:5Hα ratio) as pale yellow oil.

Method 3

10% Pd/C was charged to a stainless steel jacketed reaction vessel under an argon atmosphere; DMF was added (20 mL), followed by a solution of crude (6β, 7α, 22E)-6-ethyl-7-hydroxy-3-oxo-4,22-choladien-24-oic acid ethyl ester from Example 3 (approximately 72.6 mmol) in DMF (130 mL). The reaction mixture was cooled to −25° C. (over approximately 40 mins) with vigorous stirring (1200 rpm). The reaction vessel was evacuated and charged with hydrogen (10-12 bar) three times. The mixture was stirred for 16 h under an atmosphere of hydrogen (10-12 bar). The vessel was evacuated, purged with argon and warmed to 20° C. with stirring. TLC of the reaction mixture (1:1 Heptane:EtOAc, developed using Ceric Ammonium Molybdate or vanillin dip, Rf values: starting material=0.42, product=0.67) indicated complete consumption of the starting material. The suspension was diluted with $CH_3CN$ (120 mL) and $H_2O$ (30 mL) and the suspension filtered via a double GFA filter paper and the filter cake rinsed with $CH_3CN$ (60 mL). The mixture was telescoped to the next step without further purification. The mixture contained approximately 5% of the 5H-α isomer.

Optimisation

The hydrogenation reaction of this example proceeds via the intermediate shown below and produces both the required 5Hβ compound and its 5Hα isomer. A solvent and catalyst screen was carried out to determine reaction conditions which led to the highest yield and the highest ratios of 5Hβ isomer to 5Hα isomer.

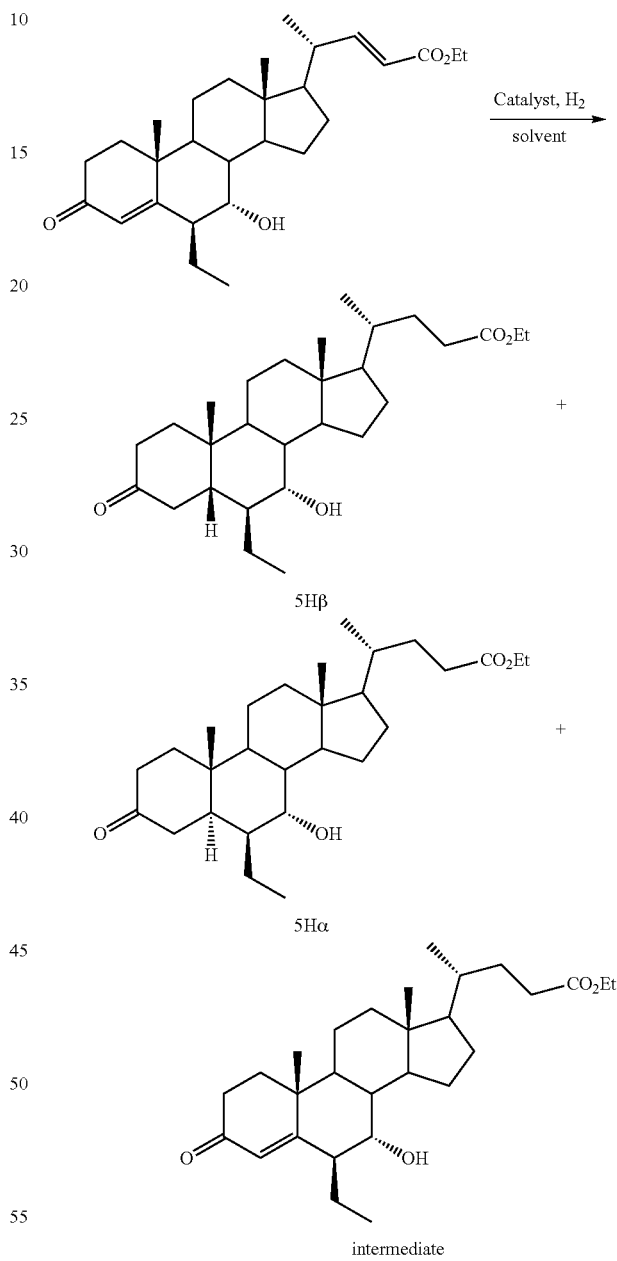

The solvent screen was performed using 10 wt. % Pd/C catalyst and the reactions were run at room temperature under atmospheric pressure of hydrogen. The reaction run in MeOH in the presence of $NEt_3$ was more selective than the one run in neat MeOH, whilst the addition of 10% of $H_2O$ decreased the 5βH selectivity. The reaction in DMF provided the best β:α ratio. The reaction in pyridine gave poor conversion to the required product with mainly starting material and intermediate present in the mixture.

|   | Solvent | 5H β:α ratio |
|---|---|---|
| A | MeOH | 4:1 |
| B | MeOH:H$_2$O | 2:1 |
| C | MeOH:NEt$_3$ | 7:1 |
| D | EtOH | 3:1 |
| E | IPA | 2:1 |
| F | EtOAc | 2:1 |
| G | Pyridine | 2:1 |
| H | AcOH | 1:1 |
| I | CPME | 1:1 |
| J | DMF | 9:1 |

Reactions in DMF and MeOH were tested at a range of temperatures. For reactions run in DMF temperature has substantial impact on selectivity (the selectivity decreases with increasing temperature), while little difference was observed for reactions in MeOH.

Reactions in DMF and MeOH were tested at a range of commercially available 5 and 10 wt. % Pd catalysts, on carbon, calcium carbonate, barium sulfate and aluminium oxide support.

The reactions were run in 10 volumes of solvent at −15° C. under atmospheric pressure of hydrogen gas. For reactions run in DMF pressure has lower impact on the selectivity than the temperature. The effect of dilution on the selectivity is negligible.

EXAMPLES 5 TO 14

Synthesis of (6β, 5β, 7α)-6-ethyl-7-hydroxy-3-oxo-cholan-24-oic acid ethyl ester from Deoxycholic Acid

EXAMPLE 5

Synthesis of (3α, 5β)-3-acetoxy-12-oxo-cholan-24-oic acid methyl ester

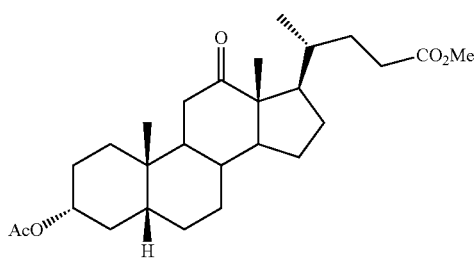 [SMILES: COC(=O)CC[C@@H](C)[C@H]1CCC2C3CC[C@@H]4C[C@H](OC(C)=O)CC[C@]4(C)C3CC(=O)[C@@]21C]

To a solution of deoxycholic acid (500 g, 1.27 mol) in MeOH (1.5 L) was charged H$_2$SO$_4$ (0.68 mL, 12.7 mmol) and the reaction heated to 64° C. until complete. The reaction was cooled to 55° C. and pyridine (2.06 mL, 25.4 mmol) was charged. MeOH (800 mL) was removed by distillation and the reaction cooled to 50° C. EtOAc (500 mL) was charged and the distillation continued. This co-evaporation was repeated until the MeOH content was <0.5%. The reaction was cooled to 40° C. and EtOAc (1.0 L) was charged followed by Pyridine (134 mL, 1.65 mol) and DMAP (1.1 g, 8.89 mmol). Acetic anhydride (150 mL, 1.58 mmol) was added dropwise and the reaction vessel stirred at 40° C. until complete. The reaction was cooled to 22° C. and 2M aq. H$_2$SO$_4$ (1500 mL) added maintaining the temperature below 25° C. The aqueous phase was removed and the organic phase washed with water (1.2 L), sat. aq. NaHCO$_3$ solution (1.2 L×2) and water (1.2 L). AcOH (1.0 L) was charged to the organic layer, followed by NaBr (6.6 g, 63.5 mmol). Aq. 16.4% NaOCl solution (958 mL, 2.54 mol) was charged dropwise maintaining the reaction temperature below 25° C. The reaction was stirred until complete, then cooled to 10° C. and stirred for 90 mins. The resulting solids were collected by filtration, washed with water (3×500 mL) and the filter cake dried under vacuum at 40° C. The solids were crystallised from MeOH (10 vol) to give (3α, 5β)-3-acetoxy-12-oxo-cholan-24-oic acid methyl ester as an off white solid (268 g).

EXAMPLE 6

Synthesis of (3α, 5β)-3-acetoxy-cholan-24-oic acid methyl ester

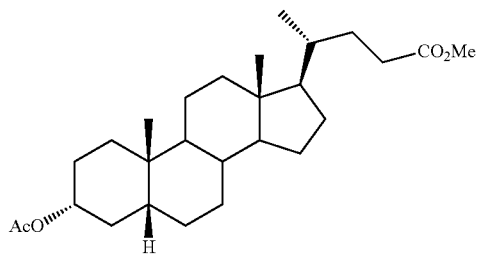 [SMILES: COC(=O)CC[C@@H](C)[C@H]1CCC2C3CC[C@@H]4C[C@H](OC(C)=O)CC[C@]4(C)C3CC[C@@]21C]

(3α, 5β)-3-acetoxy-12-oxo-cholan-24-oic acid methyl ester (268 g, 0.6 mol) was charged to the reaction vessel under argon, followed by AcOH (1.8 L). Tosyl hydrazide (190 g, 1.02 mol) was then added maintaining the reaction temperature at 25° C. The reaction was stirred until complete and then NaBH$_4$ (113.5 g, 3.00 mol) was charged portionwise maintaining the temperature below 25° C. The reaction mixture was stirred until complete and then quenched by the dropwise addition of water (1.34 L) maintaining the temperature below 25° C. The reaction mixture was stirred for 30 mins, the resulting solids collected by filtration, washed with water (3×270 mL) and the solid dried under vacuum at 40° C. The solids were crystallised from MeOH (3 vol) to give (3α, 5β)-3-acetoxy-cholan-24-oic acid methyl ester as an off white solid (214.5 g).

EXAMPLE 7

Synthesis of (3α, 5β)-3-hydroxy-cholan-24-oic acid (Lithocholic Acid)

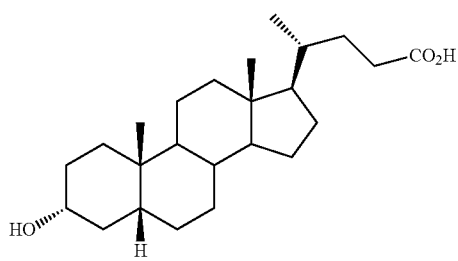 [SMILES: C[C@H](CCC(=O)O)[C@H]1CCC2C3CC[C@@H]4C[C@H](O)CC[C@]4(C)C3CC[C@@]21C]

To a solution of (3α, 5β)-3-acetoxy-cholan-24-oic acid methyl ester (214.5 g, 0.50 mol) in IPA (536 mL) was charged water (536 mL) and 50% w/w NaOH (99 g, 1.24 mol). The reaction was heated to 50° C. and stirred until complete. 2M H₂SO₄ was charged slowly with vigorous stirring until pH 2-3 was obtained and then the reaction cooled to 20° C. The resulting solids were collected by filtration, washed with water (3×215 mL) and the resultant solid dried under vacuum at 40° C. to give (3α, 5β)-3-hydroxy-cholan-24-oic acid (176.53 g)

EXAMPLE 8

Synthesis of (5β)-3-oxocholan-24-oic acid ethyl ester

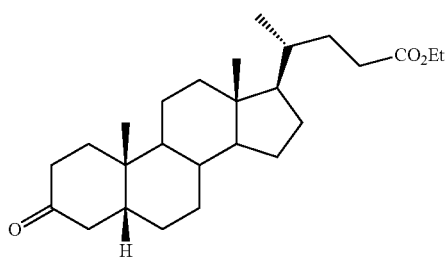 [SMILES: CCOC(=O)CC[C@@H](C)[C@H]1CCC2C3CC[C@@H]4CC(=O)CC[C@]4(C)C3CC[C@@]21C]

To a solution of (3α, 5β)-3-hydroxy-cholan-24-oic acid (10 g, 26.5 mmol) in EtOH (50 mL) was charged H₂SO₄ 96% (14 µL, 0.27 mmol) and the reaction mixture then heated to reflux for 16 h. Pyridine was then charged, the mixture stirred for 30 mins and concentrated in vacuo at 40° C. The residue was dissolved in EtOAc (30 mL) and AcOH (10 mL) and NaBr (136 mg, 1.33 mmol) was then charged. The solution was cooled to 5° C. and NaOCl 9% (27 mL, 39.8 mmol) was charged dropwise maintaining the temperature below 10° C. The resulting suspension was warmed to ambient temperature and stirred for 1 h. The reaction mixture was cooled to 0° C. for 10 mins, the solids collected by filtration and washed with water (3×3 vol). The resultant solid was dried under vacuum at 40° C. to give (5β)-3-oxocholan-24-oic acid ethyl ester (7.83 g).

EXAMPLE 9

Synthesis of (4α, 5β)-3-oxo-4-bromo-cholan-24-oic acid ethyl ester

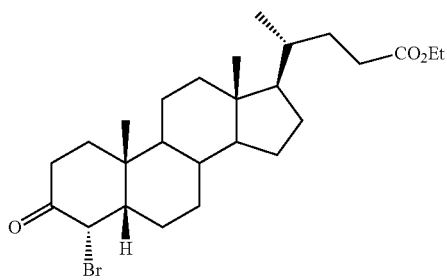 [SMILES: CCOC(=O)CC[C@@H](C)[C@H]1CCC2C3CC[C@@H]4[C@H](Br)C(=O)CC[C@]4(C)C3CC[C@@]21C]

To a solution of (5β)-3-oxocholan-24-oic acid ethyl ester (8.0 g, 19.9 mmol) in AcOH (84 mL) was added Br₂ in AcOH (16 mL, 21.9 mmol) dropwise over 15 mins. The reaction mixture was stirred for 10 mins, then diluted with EtOAc (250 mL), washed with water (2×200 mL) and concentrated in vacuo at 40° C. The crude material was purified by column chromatography (30% Heptane:EtOAc) and concentrated in vacuo at 40° C. to give (4α, 5β)-3-oxo-4-bromo-cholan-24-oic acid ethyl ester as a pale crystalline solid (7.49 g).

EXAMPLE 10

Synthesis of 3-oxo-4-cholen-24-oic acid ethyl ester

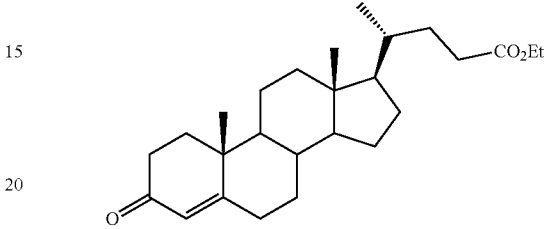

To a solution of (4α, 5β)-3-oxo-4-bromo-cholan-24-oic acid ethyl ester (4.0 g, 8.33 mmol) in DMF (40 mL) was charged Li₂CO₃ (4.0 g, 1 mass eq) and LiBr (2.0 g, 0.5 mass eq). The mixture was heated to 150° C. for 2 h then allowed to cool to ambient temperature and poured onto a mixture of water and ice (200 g, 50 volumes) and AcOH (8 mL). The resulting suspension was stirred for 15 mins, the solids collected by filtration and then purified by column chromatography (30% Heptane:EtOAc) to give 3-oxo-4-cholen-24-oic acid ethyl ester as a pale crystalline solid (1.68 g).

EXAMPLE 11

Synthesis of 3-oxo-4,6-choladien-24-oic acid ethyl ester

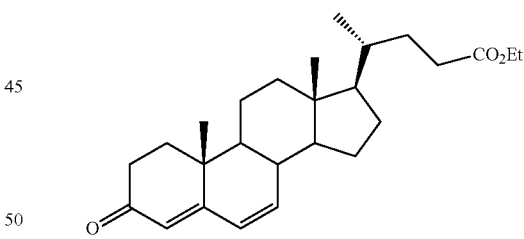

3-oxo-4-cholen-24-oic acid ethyl ester (2.23 g, 5.57 mmol) was charged to a reaction vessel, followed by AcOH (6.7 mL) and toluene (2.23 mL). Chloranil (1.5 g, 6.13 mmol) was charged and the reaction mixture heated to 100° C. for 2 h (IPC by TLC, 3:7 EtOAc: Heptane; visualized with Anisaldehyde stain). The reaction mixture was cooled to 10° C. for 10 mins and the resulting solid removed by filtration. The filter cake was washed with DCM (9 vol) and the resulting filtrate then concentrated in vacuo at 40° C. The residue was dissolved in acetone (9 vol) then 3% w/w aq. NaOH (27 vol) was added dropwise maintaining the temperature below 30° C. The resulting mixture was cooled in an ice bath for 10 mins and the solids collected by filtration. The filter cake was washed with water (2×9 vol) and acetone: water 2:1 (4 vol). Purification by column chromatography (0-30% Heptane:EtOAc) gave 3-oxo-4,6-choladien-24-oic acid ethyl ester as a pale crystalline solid (1.45 g)

EXAMPLE 12

Synthesis of (6α, 7α)-6,7-epoxy-3-oxo-4-cholen-24-oic acid ethyl ester

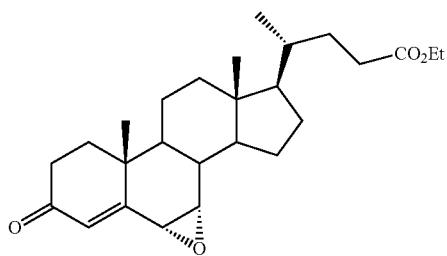 [SMILES: CCOC(=O)CC[C@@H](C)[C@H]1CCC2C3C(CC[C@@]21C)[C@@]1(C)CCC(=O)C=C1[C@H]1O[C@@H]31]

3-oxo-4,6-choladien-24-oic acid ethyl ester (1.37 g, 4.27 mmol) was charged to a reaction vessel, followed by BHT (23 mg, 0.13 mmol), EtOAc (11 mL) and water (3.4 mL) with stirring. The solution was heated to 80° C. and then a solution of mCPBA 70% (1.5 g, 7.51 mmol) in EtOAc (7.5 mL) was added dropwise over 15 mins. The reaction mixture was stirred at 70° C. for 2 h (IPC by TLC, 3:7 EtOAc:Heptane; visualized with Anisaldehyde stain), cooled to ambient temperature and then washed with 1M aq.NaOH (2×20 mL) followed by 10% aq. $NaS_2O_3$: 2% $NaHCO_3$ (3×20 mL). The organic phases were dried over $Na_2SO_4$ and concentrated in vacuo at 40° C. The crude solids were crystalized from EtOAc (3 vol) at 60° C. to give an off white solid which was dried under vacuum at 40° C. to give (6α, 7α)-6,7-epoxy-3-oxo-4-chola-ene-24-oic acid ethyl ester (0.90 g).

EXAMPLE 13

Synthesis of (6β,7α)-6-ethyl-7-hydroxy-3-oxo-4-cholen-24-oic acid ethyl ester

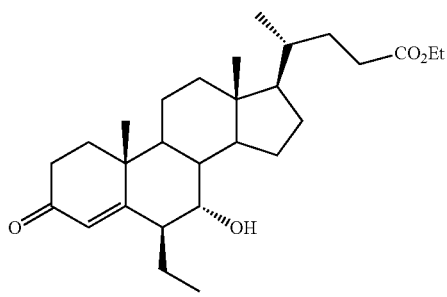 [SMILES: CCOC(=O)CC[C@@H](C)[C@H]1CCC2C3C(CC[C@@]21C)[C@@]1(C)CCC(=O)C=C1[C@H](CC)[C@H]3O]

$ZnCl_2$ (600 mg, 4.25 mmol) was charged to a reaction vessel and dried under vacuum at 180° C. for 1 h. The reaction vessel was cooled to ambient temperature, THF (15 mL) charged and the contents of the reaction vessel cooled to 3° C. A solution of 3M EtMgBr in $Et_2O$ (1.5 mL, 4.25 mmol) was charged to the reaction vessel over 40 mins maintaining the temperature below 5° C. The reaction mixture was then stirred for 1 h. (6α, 7α)-6,7-epoxy-3-oxo-4-cholen-24-oic acid ethyl ester (0.80 g, 1.93 mmol) in THF (6 mL) was charged to the reaction vessel over 40 mins, maintaining the temperature below 5° C. CuCl (20 mg, 0.19 mmol) was charged in one portion and the reaction stirred at ambient temperature for 16 h (IPC by TLC, 3:7 EtOAc:Heptane; visualized with Anisaldehyde stain). The reaction mixture was cooled in an ice bath and sat. aq.$NH_4Cl$ was added dropwise, maintaining the temperature below 10° C. The reaction mixture was filtered and the filter cake washed with TBME (12.5 vol). The organic phase of the filtrate was separated and the aqueous phase extracted with TBME (2×12.5 vol). The combined organic phases were washed with 5% NaCl (3×12.5 vol) and concentrated in vacuo at 40° C.

EXAMPLE 14

Synthesis of (6β, 5β, 7α)-6-ethyl-7-hydroxy-3-oxo-cholan-24-oic acid ethyl ester

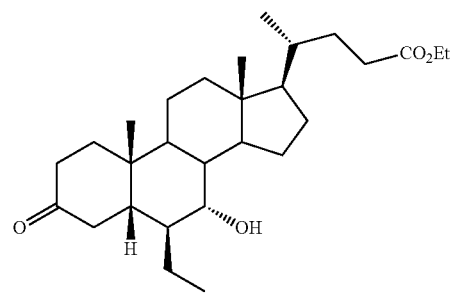 [SMILES: CCOC(=O)CC[C@@H](C)[C@H]1CCC2C3C(CC[C@@]21C)[C@@]1(C)CCC(=O)C[C@H]1[C@H](CC)[C@H]3O]

10% Pd/C (70 mg) was charged to a reaction vessel under an argon atmosphere followed by the crude material from Example 13 in DMF (14.6 mL). The mixture was cooled to −10° C. and the reaction vessel was evacuated then filled with hydrogen three times with vigorous stirring. The mixture was stirred under an atmosphere of hydrogen for 24 h while maintaining the temperature at −10° C. (IPC by TLC, eluent 1:1 EtOAc:Heptane; visualized with Anisaldehyde stain) then the flask was evacuated, filled with argon and filtered through a pad of celite and rinsed with DMF (7 mL). 10% Pd/C (70 mg) was recharged to the reaction vessel under an argon atmosphere followed by the DMF reaction mixture. The mixture was cooled to approximately −10° C. and the reaction vessel was evacuated then filled with hydrogen three times with vigorous stirring. The mixture was stirred under an atmosphere of hydrogen for 24 h at −10° C. (IPC by TLC, 1:1 EtOAc: Heptane; visualized with Anisaldehyde stain) then the flask was evacuated, filled with argon and filtered through a pad of celite and washed with TBME (62.5 vol, 50 mL). The filtrate was washed with 10% aq. NaCl (4×25 vol), dried over $Na_2SO_4$, filtered and concentrated in vacuo at 40° C. Purification by column chromatography ($SiO_2$, 0-30% Heptane:EtOAc) gave (6β, 5β, 7α)-6-ethyl-7-hydroxy-3-oxo-cholan-24-oic acid ethyl ester (0.17 g). The product was identical to the material obtained from plant origin (6β, 7α, 22E)-6-ethyl-7-hydroxy-3-oxo-4, 22-choladien-24-oic acid ethyl ester (see Example 4).

EXAMPLES 15 TO 17

Conversion of (6β, 5β, 7α)-6-ethyl-7-hydroxy-3-oxo-cholan-24-oic acid ethyl ester to (3α, 5β, 6α, 7α)-6-ethyl-3,7-dihydroxy-cholan-24-oic acid

EXAMPLE 15

Synthesis of (6β, 5β)-3,7-dioxo-6-ethyl-cholan-24-oic acid ethyl ester

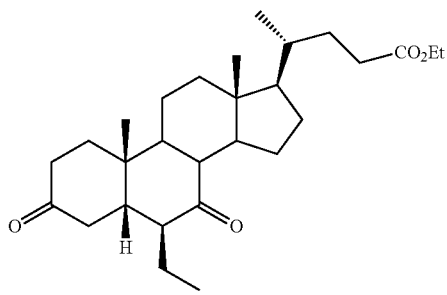 [SMILES: CCOC(=O)CC[C@@H](C)[C@H]1CCC2C3C(=O)[C@@H](CC)[C@@H]4CC(=O)CC[C@]4(C)C3CC[C@@]21C]

Method 1

A solution of Jones's reagent prepared from CrO₃ (1.10 g, 11 mmol) in H₂SO₄ (1.4 mL) and made to 5 mL with water was charged dropwise to a solution of (6β, 5β, 7α)-6-ethyl-7-hydroxy-3-oxo-cholan-24-oic acid ethyl ester (0.18 g, 0.40 mmol) in acetone (10 mL) until an orange colour persisted. The reaction mixture was quenched with IPA (1 mL), filtered through a 0.45 μm nylon syringe filter and the filter was washed with acetone (10 mL). The combined filtrate and wash was concentrated, the residue was dissolved in EtOAc (20 mL) and washed with water (2×10 mL). The aqueous phase was extracted with EtOAc (20 mL), the combined EtOAc phases were concentrated and the residue was dissolved and concentrated from toluene (20 mL) then acetone (20 mL) to give a clear oil containing (6β, 5β, 7α)-6-ethyl-7-hydroxy-3,7-dioxo-cholan-24-oic acid ethyl ester (185 mg).

$^1$H NMR (700 MHz, CDCl$_3$): δ=4.12 (2H, q, J=7.1), 2.42 (1H, t, J=11.4), 2.38-2.17 (6H, m), 2.09-1.74 (9H, m), 1.68-1.11 (17H, m), 0.93 (3H, d, J=6.5), 0.85 (3H, t, J=7.4), 0.72 (3H, s). $^{13}$C NMR (100 MHz, CDCl$_3$): δ=214.5, 211.4, 174.0, 60.1, 57.1, 55.1, 50.3, 48.4, 47.3, 44.9, 43.6, 43.1, 39.2, 35.8, 35.2 (×2), 34.9, 31.3, 30.9, 28.1, 24.6, 23.7, 23.4, 21.7, 18.3, 14.2, 12.6, 12.2. (IR) ν$_{max}$(cm$^{-1}$): 2950, 2872, 1709, 1461, 1377, 1304, 1250, 1177, 1097, 1034; HRMS (ESI-TOF) m/z: (M+H)$^+$ calcd for C$_{28}$H$_{45}$O$_4$ 445.3318; found: 445.3312;

Method 2

To a solution of (6β, 5β, 7α)-6-ethyl-7-hydroxy-3-oxo-cholan-24-oic acid ethyl ester (41.0 g crude mass) in anhydrous CH$_2$Cl$_2$ (600 mL) at 0° C. was added solid DMP (34.0 g, 80.2 mmol) portion-wise over 20 mins (exothermic). The mixture was stirred at 0-5° C. for 2 h, then a further portion of DMP (4.0 g, 9.4 mmol) was added and reaction stirred at 0-5° C. for 1 h. The mixture was filtered through a GFA filter and the solid rinsed with CH$_2$Cl$_2$ (50 mL), the filtrate was stirred vigorously with 10% aq. Na$_2$S$_2$O$_3$ and 2% aq. NaHCO$_3$ (100 mL) for 20 mins. The phases were separated and the aq. extracted with CH$_2$Cl$_2$ (2×100 mL). The combined organic extracts were washed with 1M NaOH (100 mL). The mixture was diluted with CH$_2$Cl$_2$ (300 mL) and phases separated. The organic layer was concentrated under reduced pressure and the residue (cloudy brown oil) was dissolved in TBME (600 mL) and washed with 1M NaOH (100 mL) and NaCl (3×100 mL). The organic phase was concentrated in vacuo to give a dark yellow runny oil, crude mass 38.1 g. The oil was dissolved in EtOH (400 mL) and stirred with activated charcoal (10 g) at 50° C., the mixture was then filtered, the charcoal rinsed with EtOH (200 mL) and the filtrate concentrated in vacuo to give (6β, 5β)-3,7-dioxo-6-ethyl-cholan-24-oic acid ethyl ester as a yellow oil (35.9 g).

Method 3

A solution of (6β, 5β, 7α)-6-ethyl-7-hydroxy-3-oxo-cholan-24-oic acid ethyl ester (218 mmol) in DMF (450 ml), CH$_3$CN (540 mL) and H$_2$O (90 mL) was charged into a 2 L vessel and cooled to 9° C., then AcOH (180 mL) was charged, followed by NaBr (4.1 g). A solution of sodium hypochlorite (~10.5% w/v, 450 mL) was added dropwise over 1.5 h, maintaining the internal temperature at 5-6° C., then the mixture was stirred for 5 h at 7° C. TLC of the reaction mixture indicated complete consumption of the starting material (IPC by TLC, eluent EtOAc/heptane 3:7, Rf for (6β, 5β, 7α)-6-ethyl-7-hydroxy-3-oxo-cholan-24-oic acid ethyl ester=0.34; (6β, 5β)-3,7-dioxo-6-ethyl-cholan-24-oic acid ethyl ester=0.45). A solution of aq. 10% w/v Na$_2$SO$_3$ (360 mL) was charged dropwise with vigorous stirring, maintaining the internal temperature at 8-10° C., then H$_2$O (270 mL) was added dropwise and the mixture stirred at 5° C. for 16 h. The solid was filtered and washed with H$_2$O (720 mL). The solid was then dissolved in TBME (1.1 L) and subsequently washed with an aq. NaHCO$_3$ (300 mL) and 10% brine (300 mL). The organic phase was then stirred with activated charcoal (10 g) for 20 mins at 40° C., treated with anhydrous MgSO$_4$ (5 g) and filtered via GFA filter paper, the filter cake was rinsed with TBME (50 mL) and the filtrate concentrated in vacuo to give (6β, 5β)-3,7-dioxo-6-ethyl-cholan-24-oic acid ethyl ester as light brown oil which solidifies on standing (82.7 g).

EXAMPLE 16

Synthesis of (6α, 5β)-3,7-dioxo-6-ethyl-cholan-24-oic acid

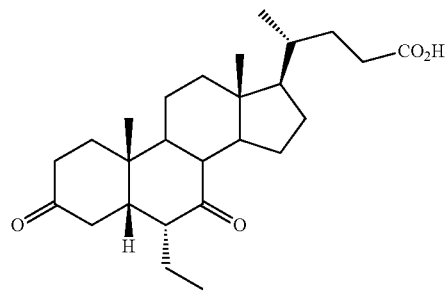 [SMILES: CC[C@H]1C(=O)C2C3CC[C@H]([C@H](C)CCC(=O)O)[C@@]3(C)CCC2[C@@]2(C)CCC(=O)C[C@@H]12]

Figure 2:
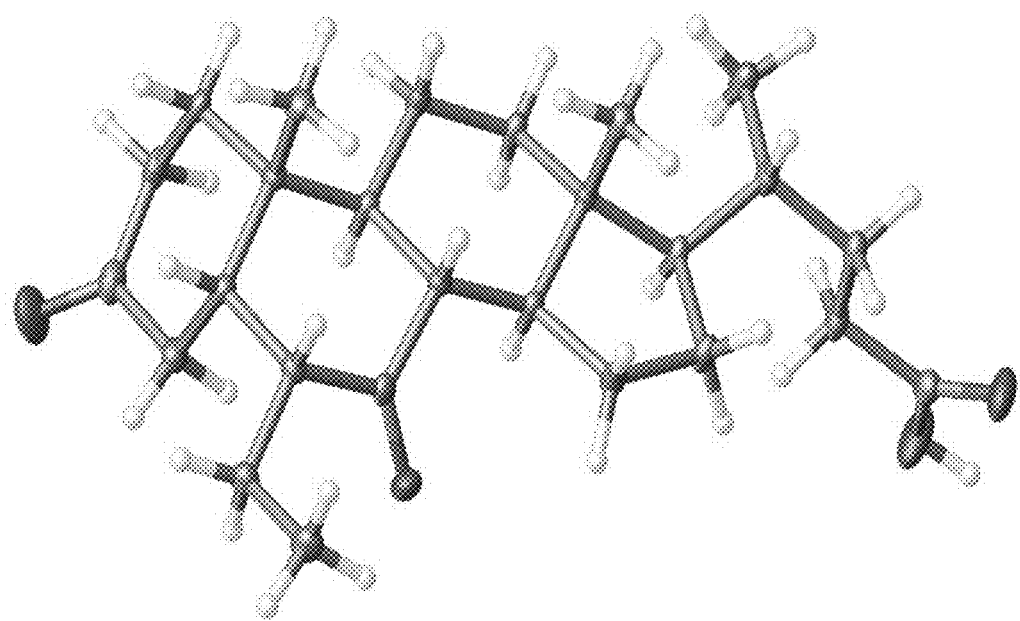
FIG. 2 is an image showing the chemical structure of (6α, 5β)-3,7-dioxo-6-ethyl-cholan-24-oic acid.

Into a 500 mL flask was charged 0.5 vol of 0.5 M NaOH (9 mL) followed by (6β, 5β)-3,7-dioxo-6-ethyl-cholan-24-oic acid ethyl ester from Example 15 (18.00 g, 1 eq) and then IPA (180 mL, 10 vol) (the initial NaOH charge was to avoid the possibility of C3-ketal formation). The mixture was warmed to 60±2° C. and held until a solution was obtained (10-15 mins). The remaining 0.5 M NaOH solution (171 mL, 9.5 vol) was charged over 20 mins and then the reaction was stirred for a further 3.5 h at 60±2° C. The IPA was removed under vacuum at 60° C. and then 2M HCl (8 mL) charged to pH 9. EtOAc was charged (90 mL, 5 vol) followed by 2M HCl (54 mL) to pH 1. Vigorous mixing was followed by phase separation. The aqueous phase was back extracted with additional EtOAc (90 mL, 5 vol) and then the combined organic phases were washed with water (54 mL, 3 vol), followed by three portions of 10% aq. NaCl (3×54 mL, 3×3 vol). The organic phase was treated with activated charcoal (100 mesh powder, 3.37 g, ~0.20 mass eq) for 12 mins and then filtered through GF/B. Concentration at 50° C. in vacuo gave (6α, 5β)-3,7-dioxo-6-ethyl-cholan-24-oic acid (FIG. 2) as a light yellow foam in quantitative yield.

$^1$H NMR (700 MHz, CDCl$_3$): δ=2.74 (1H, dd, J=12.8, 5.4), 2.47 (1H, t, J=12.5), 2.43-0.90 (32H, m), 0.81 (3H, t, J=7.4), 0.70 (3H, s). $^{13}$C NMR (100 MHz, CDCl$_3$): δ=212.1, 210.6, 179.4, 54.9, 52.4, 52.3, 50.0, 48.9, 43.7, 42.7, 38.9, 38.3, 36.7, 36.0, 35.5, 35.2, 30.9, 30.7, 28.2, 24.6, 22.9, 22.3, 18.6, 18.3, 12.1, 11.8. (IR) $v_{max}$(cm$^{-1}$): 2939, 2873, 1706, 1458, 1382, 1284.8. HRMS (ESI-TOF) m/z: (M+H)$^+$ calcd for C$_{26}$H$_{41}$O$_4$ 417.3005; found: 417.2997; mp=71.2-75.9° C.

EXAMPLE 17

Synthesis of (3α, 5β, 6α, 7α)-6-ethyl-3,7-dihydroxy-cholan-24-oic acid

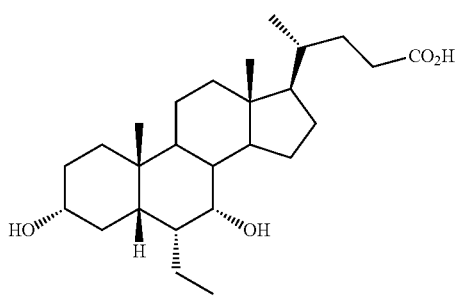 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

To a solution of crude (6α, 5β)-6-ethyl-3,7-dioxo-cholan-24-oic acid (21.7 g crude mass) in H$_2$O (260 mL) and 50% NaOH (15.2 mL) at 90° C. was added, dropwise, a solution of NaBH$_4$ (4.4 g, 116.3 mmol) in aq. NaOH (prepared from 25 mL of H$_2$O and 0.8 mL 50% NaOH). The mixture was heated to reflux and stirred for 3 h. The mixture was then cooled to 60° C. and a 2M solution of HCl (200 mL) added dropwise with vigorous stirring. nBuOAc (100 mL) was then charged to the reaction flask and the mixture stirred for a further 20 mins. The phases were separated and the aqueous phase (pH=1/2) extracted with nBuOAc (100 mL). The combined organic phases were washed with 2M HCl (50 mL) and 10% aq. NaCl (100 mL). The organic solvent was distilled off under reduced pressure at 70-80° C. The residue (dense oil) was dissolved in nBuOAc (60 mL) at 70° C. and allowed to gradually cool to room temperature, then stored at 6° C. for 2 h. The solid was collected via filtration, rinsed with cold nBuOAc (20 mL), then dried under vacuum at 70° C. for 5h to give (3α, 5β, 6α, 7α)-6-ethyl-3,7-dihydroxy-cholan-24-oic acid as a white solid (8.2 g).

The invention claimed is:

1. A compound of general formula (I):

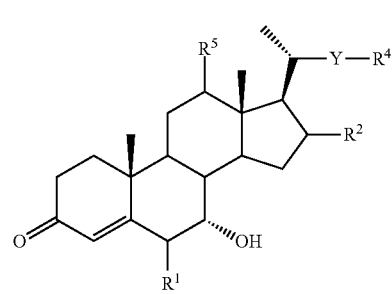

wherein:

R$^1$ is C$_{1-4}$ alkyl optionally substituted with one or more substituents selected from halo, OR$^6$ or NR$^6$R$^7$; where each of R$^6$ and R$^7$ is independently selected from H or C$_{1-4}$ alkyl;

R$^2$ is H, halo or OH or a protected OH;

Y is a bond or an alkylene, alkenylene or alkynylene linker group having from 1 to 20 carbon atoms and optionally substituted with one or more groups R$^3$;

each R$^3$ is independently halo, OR$^8$ or NR$^8$R$^9$;

where each of R$^8$ and R$^9$ is independently selected from H or C$_{1-4}$ alkyl; and R$^4$ is C(O)OR$^{10}$, OC(O)R$^{10}$, C(O)NR$^{10}$R$^{11}$, OR$^{10}$, OSi(R$^{13}$)$_3$, S(O)R$^{10}$, SO$_2$R$^{10}$, OSO$_2$R$^{10}$, SO$_3$R$^{10}$, or OSO$_3$R$^{10}$;

where each R$^{10}$ and R$^{11}$ is independently:

a. hydrogen or b. C$_{1-20}$ alkyl, C$_{2-20}$ alkenyl, C$_{2-20}$ alkynyl, —O—C$_{1-20}$ alkyl, —O—C$_{2-20}$ alkenyl or —O—C$_{2-20}$ alkynyl, any of which is optionally substituted with one or more substituents selected from halo, NO$_2$, CN, OR$^{19}$, SR$^{19}$, SO$_2$R$^{19}$, SO$_3$R$^{19}$ or N(R$^{19}$)$_2$, or a 6- to 14-membered aryl or 5 to 14-membered heteroaryl group, either of which is optionally substituted with C$_{1-6}$ alkyl, C$_{1-6}$ haloalkyl, halo, NO$_2$, CN, OR$^{19}$, SR$^{19}$, SO$_2$R$^{19}$, SO$_3$R$^{19}$ or N(R$^{19}$)$_2$; or c. a 6- to 14-membered aryl or 5 to 14-membered heteroaryl group either of which is optionally substituted with one or more substituents selected from C$_{1-6}$ alkyl, C$_{1-6}$ haloalkyl, halo, NO$_2$, CN, OR$^{19}$, SR$^{19}$, SO$_2$R$^{19}$, SO$_3$R$^{19}$ or N(R$^{19}$)$_2$;

d. a polyethylene glycol residue;

each R$^{19}$ is independently selected from H, C$_{1-6}$ alkyl, C$_{1-6}$ haloalkyl, or a 6- to 14-membered aryl or 5 to 14-membered heteroaryl group either of which is optionally substituted with halo, C$_{1-6}$ alkyl or C$_{1-6}$ haloalkyl;

each R$^{13}$ is independently a. C$_{1-20}$ alkyl, C$_{2-20}$ alkenyl or C$_{2-20}$ alkynyl optionally substituted with one or more substituents selected from halo, NO$_2$, CN, OR$^{19}$, SR$^{19}$, SO$_2$R$^{19}$, SO$_3$R$^{19}$ or N(R$^{19}$)$_2$, a 6- to 14-membered aryl or 5 to 14-membered heteroaryl group, either of which is optionally substituted with C$_{1-6}$ alkyl, C$_{1-6}$ haloalkyl, halo, NO$_2$, CN, OR$^{19}$, SO$_2$R$^{19}$, SO$_3$R$^{19}$ or N(R$^{19}$)$_2$; or b. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;

each $R^{19}$ is independently selected from H, $C_{1-6}$ alkyl or $C_{1-6}$ haloalkyl;

$R^5$ is H or OH or a protected OH;

or a salt thereof.

2. A compound according to claim 1 wherein the compound of general formula (I) is a compound of general formula (IA):

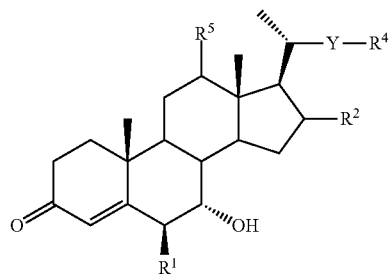

(IA)

wherein $R^1$, $R^2$, Y, $R^4$ and $R^5$ are as defined for general formula (I).

3. A compound according to claim 1 wherein $R^1$ is ethyl.

4. A compound according to claim 1 wherein Y is an alkylene or alkenylene linker group having from 1 to 8 carbon atoms and optionally substituted with one or more groups $R^3$, wherein $R^3$ is as defined in claim 1.

5. A compound according to claim 1 wherein:

Y is a bond or an alkylene or alkenylene group having 1 to 3 carbon atoms and is optionally substituted with one or two $R^3$ groups; and/or $R^4$ is $C(O)OR^{10}$, $SO_3R^{10}$, or $OSO_3R^{10}$, where $R^{10}$ is H, $C_{1-6}$ alkyl or benzyl; and/or $R^5$ is H or OH.

6. A compound according to claim 5 wherein:

$R^1$ is ethyl; and/or $R^2$ is H; and/or

Y is a bond, —$CH_2$—, —$CH_2CH_2$—, —CH=CH— or —CH=C($CH_3$)—; and/or $R^4$ is $C(O)OR^{10}$, where $R^{10}$ is H, $C_{1-6}$ alkyl or benzyl; and/or $R^5$ is H.

7. A compound according to claim 6 wherein $R^1$ is ethyl and/or $R^{10}$ is $C_{1-6}$ alkyl or benzyl.

8. A compound according to claim 1 selected from:

(6β, 7α, 22E)-6-ethyl-7-hydroxy-3-oxo-4,22-choladien-24-oic acid;

(6β, 7α)-6-ethyl-7-hydroxy-3-oxo-4-cholen-24-oic acid and $C_{1-6}$ alkyl and benzyl esters thereof and salts thereof.

9. A process for the preparation of a compound of general formula (I):

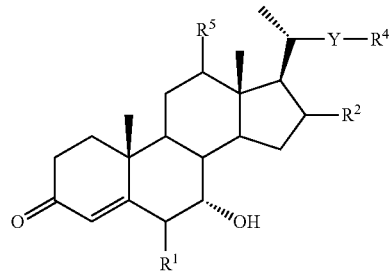

(I)

wherein:
$R^1$ is $C_{1-4}$ alkyl optionally substituted with one or more substituents selected from halo, $OR^6$ or $NR^6R^7$; where each of $R^6$ and $R^7$ is independently selected from H or $C_{1-4}$ alkyl;

$R^2$ is H, halo or OH or a protected OH;

Y is a bond or an alkylene, alkenylene or alkynylene linker group having from 1 to 20 carbon atoms and optionally substituted with one or more groups $R^3$;

each $R^3$ is independently halo, $OR^8$ or $NR^8R^9$; where each of $R^8$ and $R^9$ is independently selected from H or $C_{1-4}$ alkyl; and $R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, or $OSO_3R^{10}$; where each $R^{10}$ and $R^{11}$ is independently:
a. hydrogen or
b. $C_{1-20}$ alkyl, $C_{2-20}$ alkenyl, $C_{2-20}$ alkynyl, —O—$C_{1-20}$ alkyl, —O—$C_{2-20}$ alkenyl or —O—$C_{2-20}$ alkynyl, any of which is optionally substituted with one or more substituents selected from halo, $NO_2$, CN, $OR^{19}$, $SR^{19}$, $SO_2R^{19}$, $SO_3R^{19}$ or $N(R^{19})_2$, or a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$; or
c. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;
d. a polyethylene glycol residue;

each $R^{19}$ is independently selected from H, $C_{1-6}$ alkyl, $C_{1-6}$ haloalkyl, or a 6- to 14-membered aryl or 5 to 14-membered heteroaryl group either of which is optionally substituted with halo, $C_{1-6}$ alkyl or $C_{1-6}$ haloalkyl;

each $R^{13}$ is independently
a. $C_{1-20}$ alkyl, $C_{2-20}$ alkenyl or $C_{2-20}$ alkynyl optionally substituted with one or more substituents selected from halo, $NO_2$, CN, $OR^{19}$, $SR^{19}$, $SO_2R^{19}$, $SO_3R^{19}$ or $N(R^{19})_2$, a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; or
b. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;

each $R^{19}$ is independently selected from H, $C_{1-6}$ alkyl or $C_{1-6}$ haloalkyl;

$R^5$ is H or OH or a protected OH;

the process comprising
selective alkylation of a compound of general formula (II):

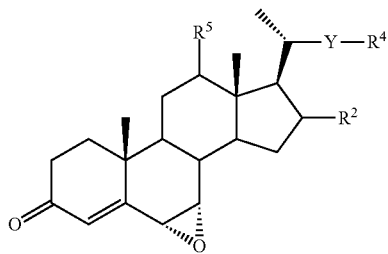
(II)

with an organometallic reagent.

10. A process according to claim 9 wherein, in Step (A), the organometallic reagent is a Gilman reagent formed by reaction of an alkyl lithium compound of formula (XXIV):

$R^1$—Li  (XXIV)

wherein $R^1$ is as defined for general formula (I);
and a copper (I) salt; or
the organometallic reagent is a Grignard reagent $R^1MgX$, where $R^1$ is as defined for general formula (I) and X is a halide and wherein the reaction is conducted in the presence of a zinc (II) salt and a catalytic amount of a copper (I) or copper(II) salt or complex.

11. A process for the preparation of a compound of general formula (XVIII):

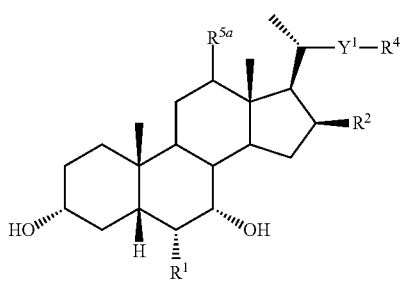
(XVIII)

wherein
$R^1$ is $C_{1-4}$ alkyl optionally substituted with one or more substituents selected from halo, $OR^6$ or $NR^6R^7$; where each of $R^6$ and $R^7$ is independently selected from H or $C_{1-4}$ alkyl;
$R^2$ is H, halo or OH; $R^{5a}$ is H or OH; and
$Y^1$ is a bond or an alkylene linker group having from 1 to 6 carbon atoms and optionally substituted with one or more group $R^3$; wherein each $R^3$ is independently halo, $OR^8$ or $NR^8R^9$; and $R^4$ is $C(O)OR^{10}$, $OC(O)R^{10}$, $C(O)NR^{10}R^{11}$, $OR^{10}$, $OSi(R^{13})_3$, $S(O)R^{10}$, $SO_2R^{10}$, $OSO_2R^{10}$, $SO_3R^{10}$, or $OSO_3R^{10}$;
where each $R^{10}$ and $R^{11}$ is independently:
a. hydrogen or
b. $C_{1-20}$ alkyl, $C_{2-20}$ alkenyl, $C_{2-20}$ alkynyl, —O—$C_{1-20}$ alkyl, —O—$C_{2-20}$ alkenyl or —O—$C_{2-20}$ alkynyl, any of which is optionally substituted with one or more substituents selected from halo, $NO_2$, CN, $OR^{19}$, $SR^{19}$, $SO_2R^{19}$, $SO_3R^{19}$ or $N(R^{19})_2$, or a 6- to 14-membered aryl or 5 to 14-membered heteroaryl group, either of which is optionally substituted with $C_{1-6}$alkyl, $C_{1-6}$ haloalkyl, halo, $NO_2$, CN, $OR^{19}$, $SR^{19}$, $SO_2R^{19}$, $SO_3R^{19}$ or $N(R^{19})_2$; or c. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;

d. a polyethylene glycol residue;

each $R^{19}$ is independently selected from H, $C_{1-6}$ alkyl, $C_{1-6}$ haloalkyl, or a 6- to 14-membered aryl or 5 to 14-membered heteroaryl group either of which is optionally substituted with halo, $C_{1-6}$ alkyl or $C_{1-6}$ haloalkyl;

each $R^{13}$ is independently
a. $C_{1-20}$ alkyl, $C_{1-20}$ alkenyl or $C_{1-20}$ alkynyl optionally substituted with one or more substituents selected from halo, $NO_2$, CN, $OR^{19}$, $SR^{19}$, $SO_2R^{19}$, $SO_3R^{19}$ or $N(R^{19})_2$, a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; or b. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;

each $R^{19}$ is independently selected from H, $C_{1-6}$ alkyl or $C_{1-6}$ haloalkyl;

the process comprising:
i. reducing a compound according to general formula (I):

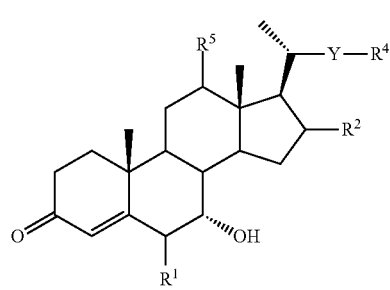
(I)

wherein:
$R^2$ is H, halo or OH or a protected OH;
Y is a bond or an alkylene, alkenylene or alkynylene linker group having from 1 to 20 carbon atoms and optionally substituted with one or more groups $R^3$;
each $R^3$ is independently halo, $OR^8$ or $NR^8R^9$;
where each of $R^8$ and $R^9$ is independently selected from H or $C_{1-4}$ alkyl;
and
$R^5$ is H or OH or a protected OH;

to give a compound of general formula (XIX):

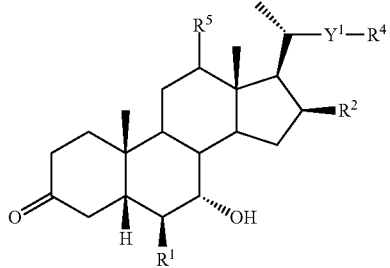

(XIX)

wherein R² is H, halo or OH or a protected OH; and
R⁵ is H or OH or a protected OH;
ii. oxidising the compound of general formula (XIX) to give a compound of general formula (XX):

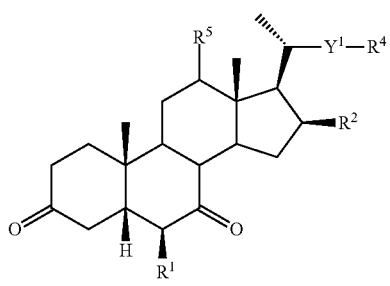

(XX)

wherein R² is H, halo or OH or a protected OH; and
R⁵ is H or OH or a protected OH;
iii. epimerisation of the compound of general formula (XX) to give a compound of general formula (XXI):

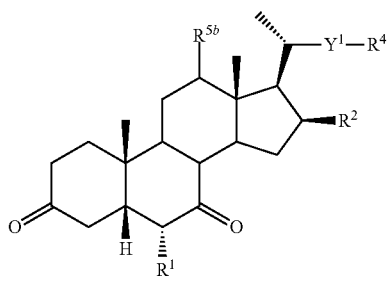

(XXI)

wherein
R² is H or OH or a protected OH group which is stable under basic conditions; and
R⁵b is H or OH or a protected OH group which is stable under basic conditions; and
(iv) reduction of the compound of general formula (XXI) and, where R² and/or R⁵ᵇ is a protected OH, removal of the protecting group(s), to give a compound of general formula (XVIII) as defined above, wherein removal of the protecting group can take place before or after the reduction; and optionally
(v) conversion of a compound of general formula (XVIII) to another compound of general formula (XVIII).

12. A process according to claim 11 wherein, in step (i), the reducing agent for the conversion of the compound of general formula (I) to the compound of general formula (XIX) is hydrogen in the presence of a palladium/carbon, palladium/calcium carbonate, palladium/aluminium oxide, platinum/palladium or Raney nickel catalyst.

13. A process according to claim 11 wherein, in step (i), the solvent is an alcoholic solvent; ethyl acetate; pyridine; acetic acid; cyclopentyl methyl ether (CPME) or N,N-dimethylformamide (DMF), any of which may optionally be mixed with a co-solvent such as acetone or water and/or a base such as triethylamine.

14. A process according to claim 11 wherein, in step (ii), the oxidation reaction is carried out using a Dess-Martin periodinane (1,1,1-triacetoxy-1,1-dihydro-1,2-benziodoxol); a hypochlorite under acidic conditions; a Jones reaction using sodium dichromate, chromic trioxide in dilute sulfuric acid; or TEMPO ((2,2,6,6-Tetramethyl-piperidin-1-yl)oxy) or a derivative thereof.

15. A process according to claim 11 wherein, in the epimerization reaction of step (iii), the compound of general formula (XX) is dissolved in an alcoholic solvent, optionally mixed with water and contacted with sodium or potassium hydroxide or a sodium or potassium alkoxide.

16. A process according to claim 15 wherein:
in the compound of general formula (XX), R⁴ is C(O)OR¹⁰, the base is sodium or potassium hydroxide and the epimerization is accompanied by hydrolysis to give a compound of general formula (XXI) in which R⁴ is C(O)OH; and/or
in the compound of general formula (XX), R² and/or R⁵ is a group OC(O)OR¹⁴, where R¹⁴ is $C_{1-6}$ alkyl or benzyl; and the epimerisation step yields a compound of general formula (XXI) in which R² and/or R⁵ᵇ is OH; or
in the compound of general formula (XX), R² and/or R⁵ is a protected OH which is stable under basic conditions and the process further comprises the step of removing the protecting group before or after step (iv).

17. A process according to claim 11 wherein, in step (iv), the reducing agent is a hydride.

18. A process according to claim 11 for the preparation of a compound of general formula (XVIII) wherein R¹ is ethyl, R² and R⁵ᵃ are both H, Y¹ is —CH₂CH₂—, and R⁴ is C(O)OH.

* * * * *